United States Patent
Kalbfeld et al.

(10) Patent No.: US 8,662,092 B2
(45) Date of Patent: Mar. 4, 2014

(54) DISPENSER FOR MULTI-TEXTURE FLOSS

(75) Inventors: Russell G. Kalbfeld, Naperville, IL (US); David L. Barcus, Elmhurst, IL (US); Chad Misner, Arlington Heights, IL (US)

(73) Assignee: Sunstar Americas, Inc., Chicago, IL (US)

( * ) Notice: Subject to any disclaimer, the term of this patent is extended or adjusted under 35 U.S.C. 154(b) by 0 days.

(21) Appl. No.: 13/341,253

(22) Filed: Dec. 30, 2011

(65) Prior Publication Data

US 2012/0160951 A1  Jun. 28, 2012

Related U.S. Application Data

(63) Continuation-in-part of application No. 12/975,151, filed on Dec. 21, 2010, now Pat. No. 8,443,817, which is a continuation-in-part of application No. 12/355,497, filed on Jan. 16, 2009.

(60) Provisional application No. 61/024,955, filed on Jan. 31, 2008.

(51) Int. Cl.
*A61C 15/00* (2006.01)

(52) U.S. Cl.
USPC .......................................................... 132/325

(58) Field of Classification Search
USPC ................... 132/324–327; D28/66
See application file for complete search history.

(56) References Cited

U.S. PATENT DOCUMENTS

| | | | |
|---|---|---|---|
| 3,747,611 A * | 7/1973 | Bennington | 132/325 |
| 3,837,351 A | 9/1974 | Thornton | |
| 3,896,824 A | 7/1975 | Thornton | |
| 4,008,727 A | 2/1977 | Thornton | |
| 4,052,994 A | 10/1977 | Thun | |
| 4,941,487 A * | 7/1990 | VanBeneden | 132/323 |
| 4,947,880 A | 8/1990 | Tarrson et al. | |
| 5,159,943 A * | 11/1992 | Richards et al. | 132/321 |

(Continued)

FOREIGN PATENT DOCUMENTS

| CA | 2129422 | 1/1999 |
|---|---|---|
| WO | 2004/034922 | 4/2004 |

OTHER PUBLICATIONS

PCT/US2012/072076 International Search Report and Written Opinion dated Mar. 13, 2013 (11 pages).

(Continued)

*Primary Examiner* — Rachel Steitz
(74) *Attorney, Agent, or Firm* — Michael Best & Friedrich LLP

(57) ABSTRACT

A dental floss dispensing unit includes a housing, a supply spool, and a metering element. The supply spool is coupled to the housing and has a length of floss wound thereabout. The length of floss has a free end extending from the housing and a plurality of alternating and distinct first and second floss segments. The metering element engages the length of floss and provides resistance to removal of the length of floss from the housing. A magnitude of the resistance changes as each floss segment moves into engagement with the metering element, thereby providing a tactilely detectable indication to the user that one of the first or second segments is emerging from the housing. The dispensing unit is configured to allow the supply spool to be manually rotated without manipulation (e.g., disassembly) of the housing for rewinding floss onto the spool.

23 Claims, 36 Drawing Sheets

(56) References Cited

U.S. PATENT DOCUMENTS

| | | |
|---|---|---|
| 5,199,452 A | 4/1993 | Cheng |
| 5,311,890 A | 5/1994 | Thornton |
| 5,353,820 A | 10/1994 | Suhonen et al. |
| 5,365,874 A * | 11/1994 | Dorfman .................. 116/200 |
| 5,433,226 A | 7/1995 | Burch |
| 5,573,022 A | 11/1996 | Winters |
| 5,718,251 A | 2/1998 | Gray et al. |
| 5,765,576 A | 6/1998 | Dolan et al. |
| 5,842,489 A | 12/1998 | Suhonen et al. |
| 7,213,604 B2 * | 5/2007 | Romine .................... 132/325 |
| 7,841,350 B2 * | 11/2010 | Kernot ..................... 132/325 |
| 2006/0225764 A1 * | 10/2006 | Mark ....................... 132/321 |
| 2006/0237028 A1 | 10/2006 | Hamidy |
| 2011/0088717 A1 | 4/2011 | Kalbfelo et al. |

OTHER PUBLICATIONS

Office Action from the United States Patent and Trademark Office for U.S. Appl. No. 12/975,151 dated Oct. 12, 2012.

* cited by examiner

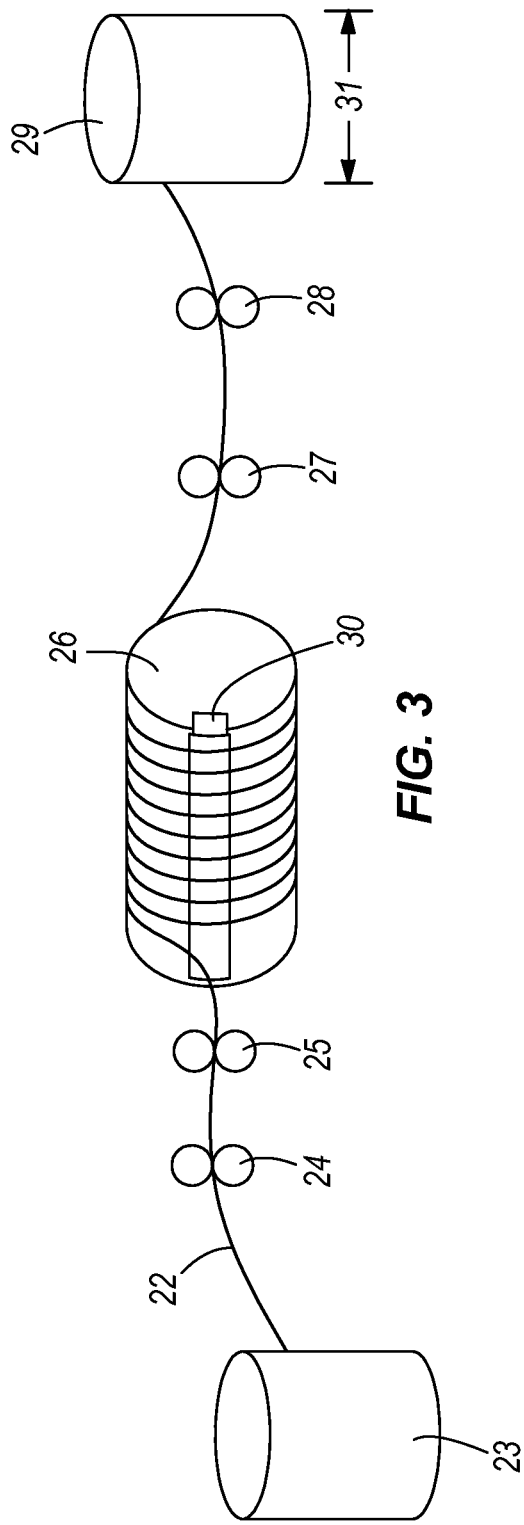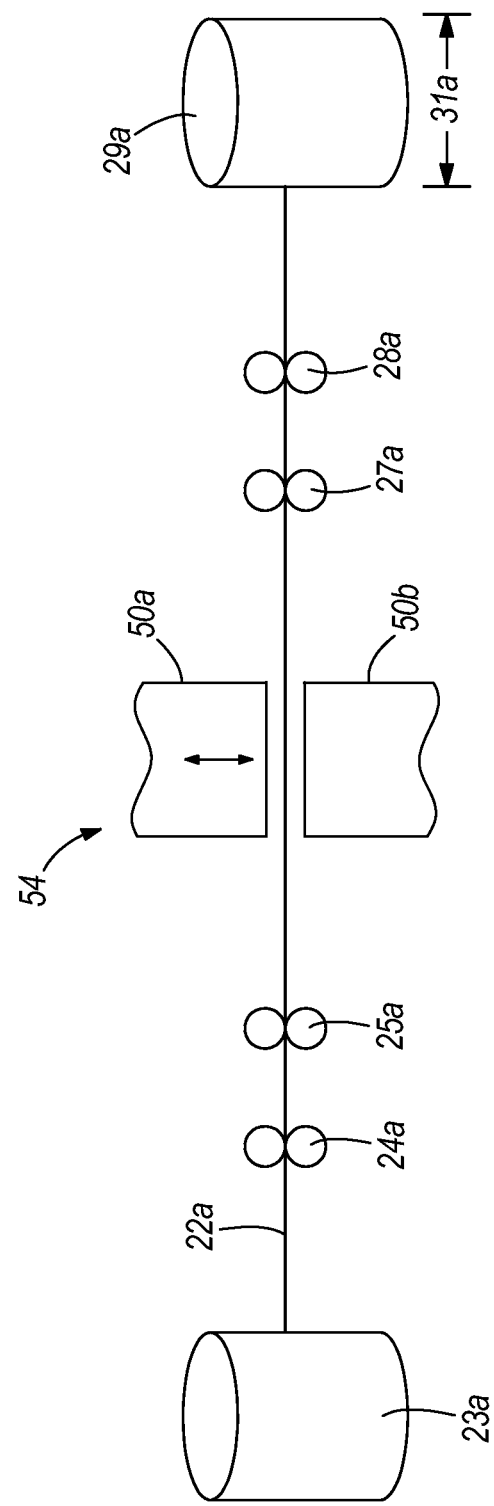

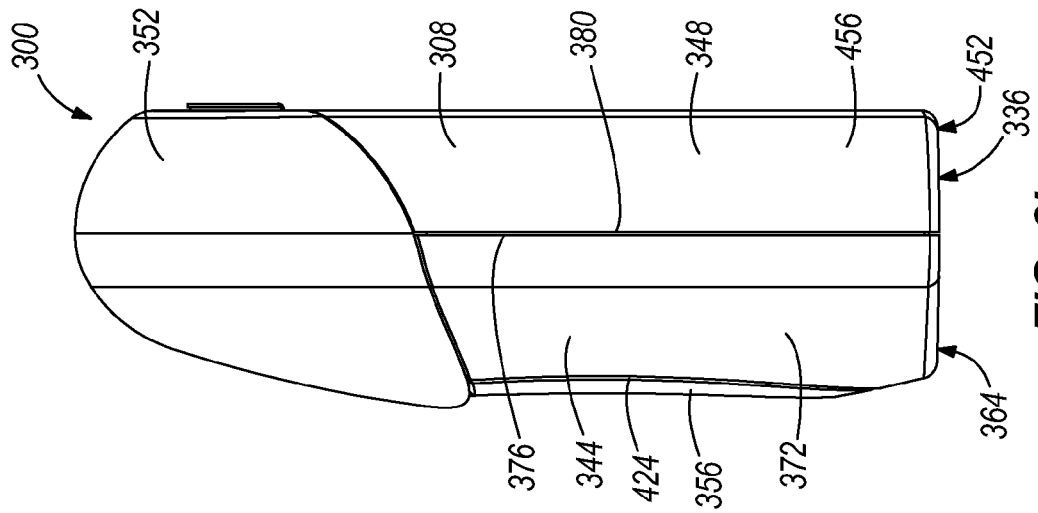
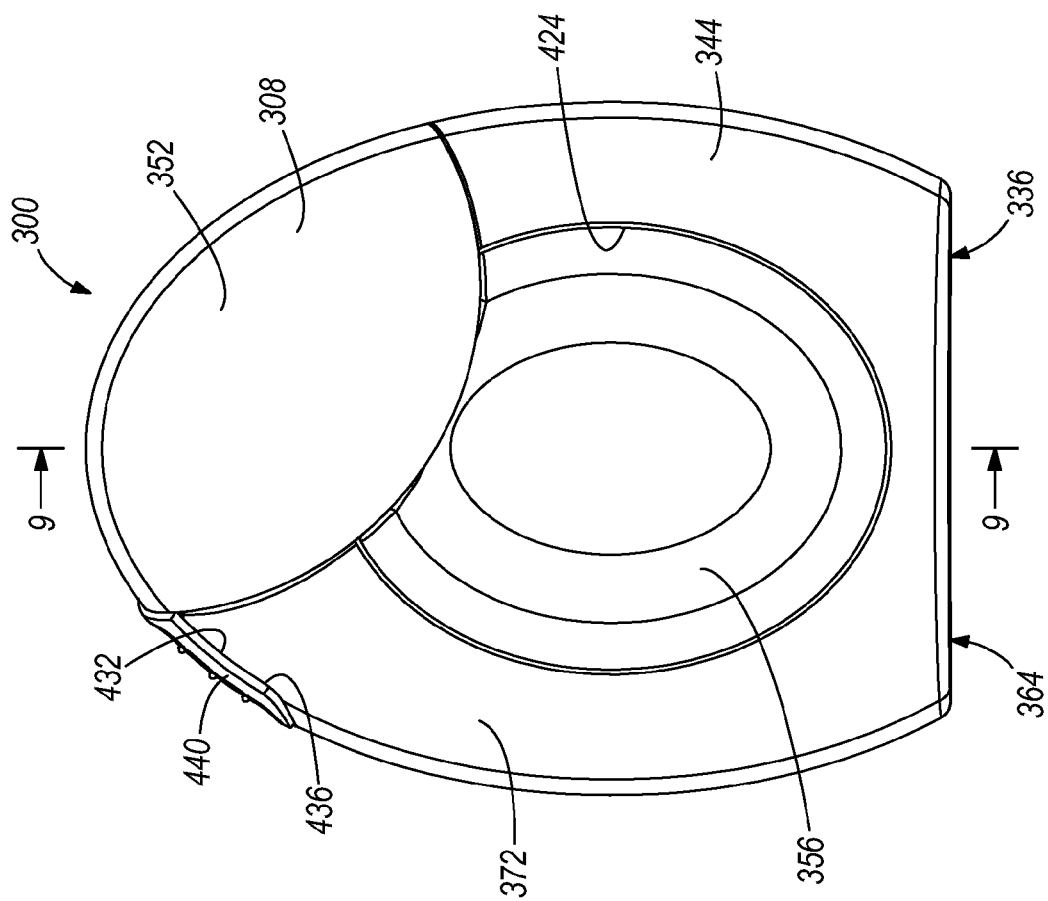

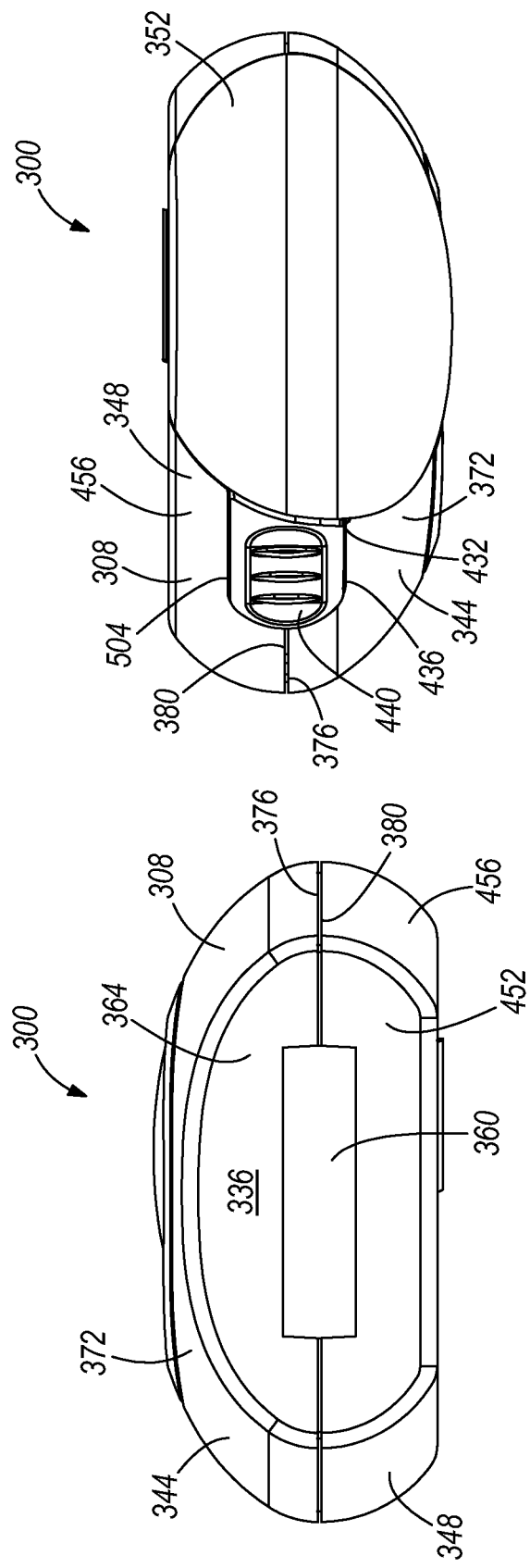

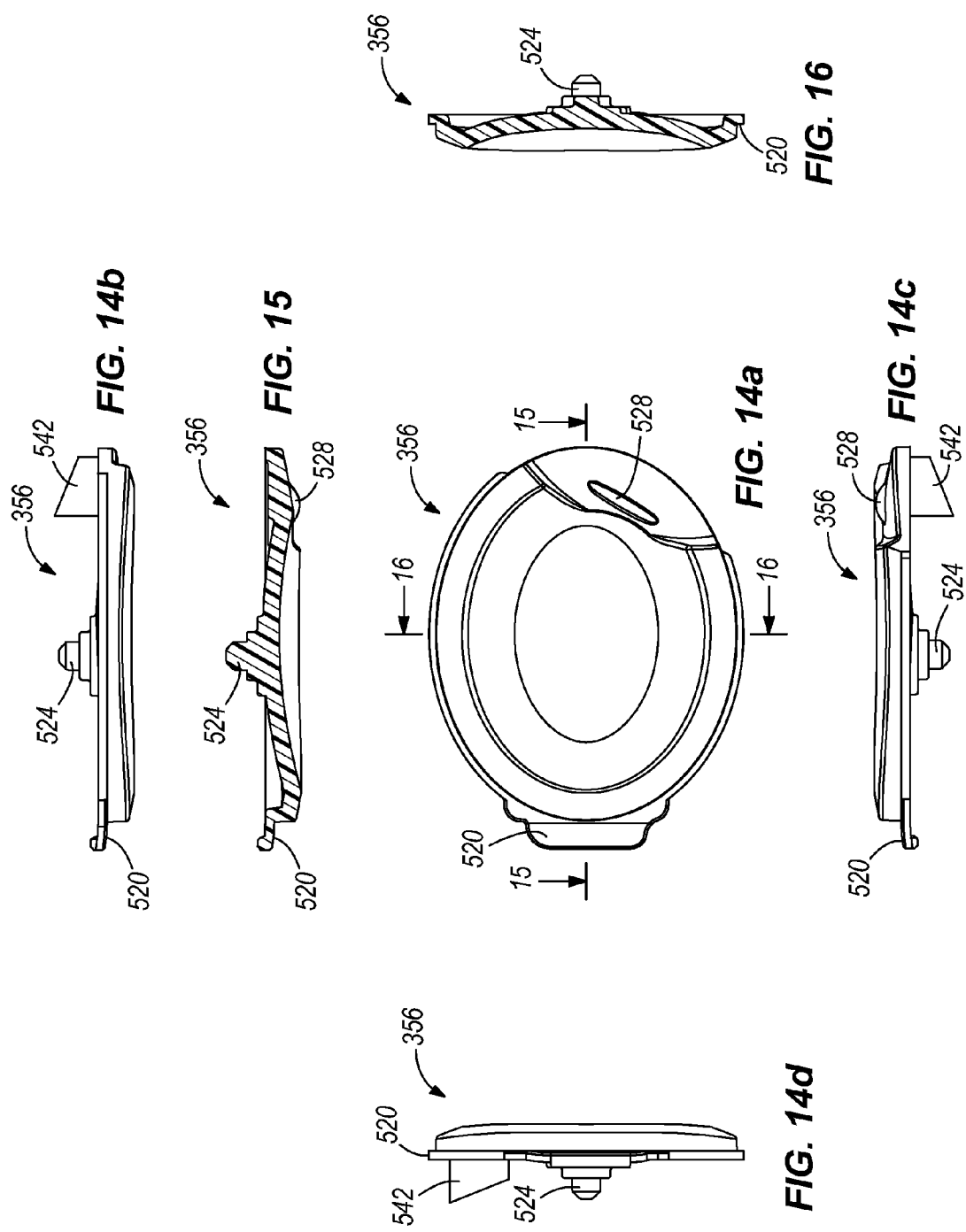

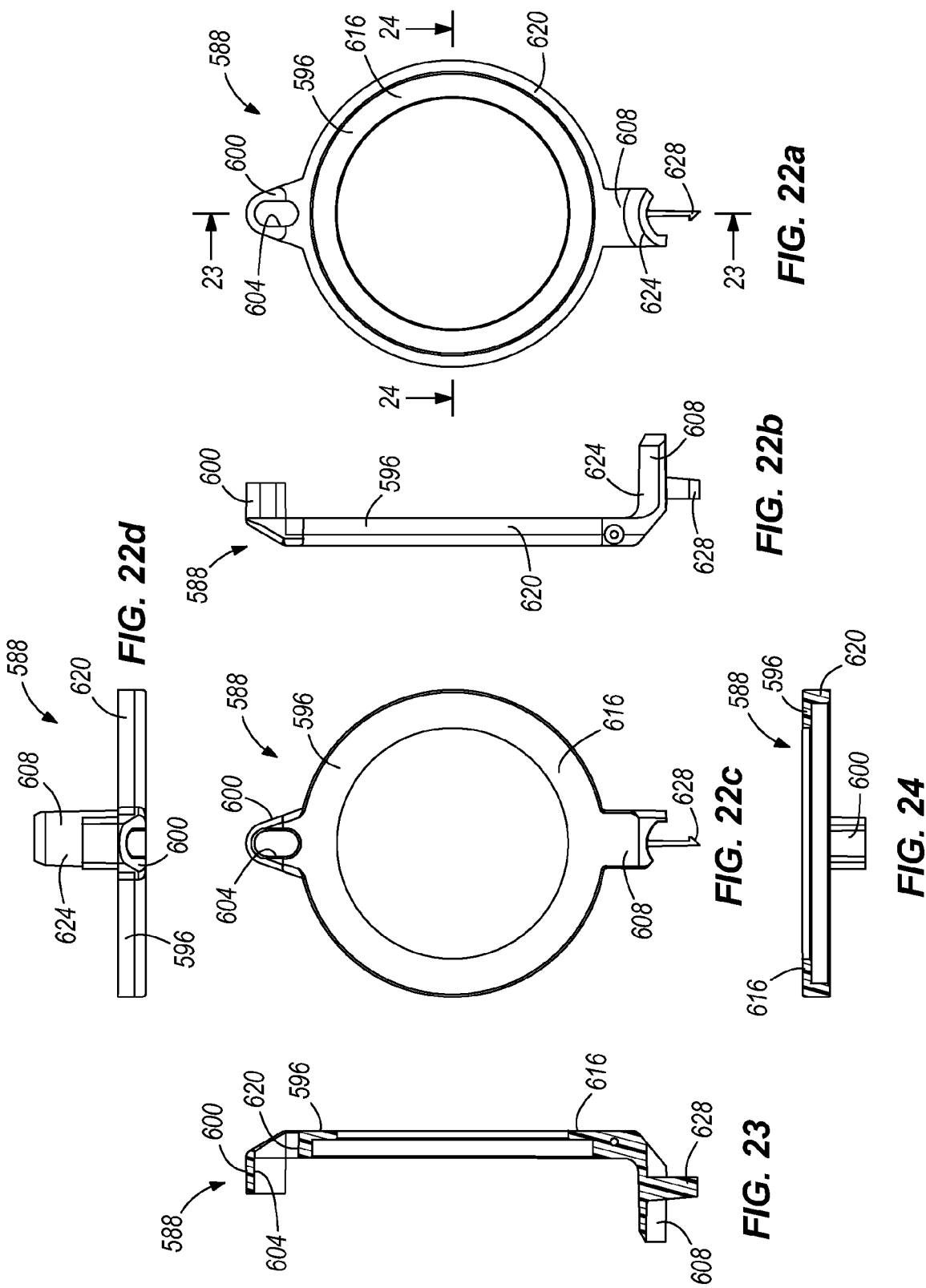

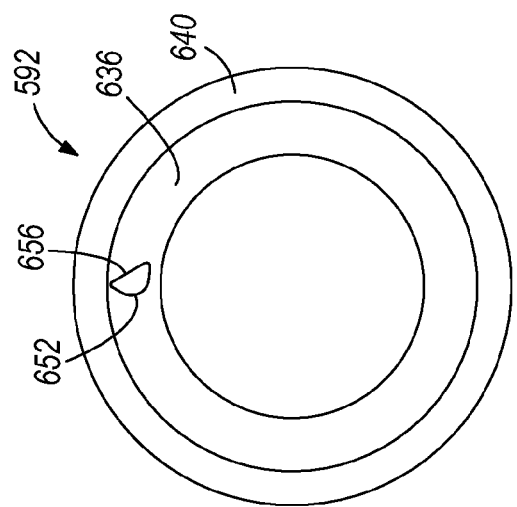
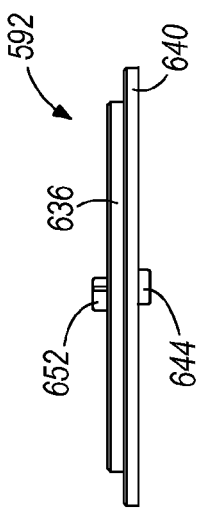
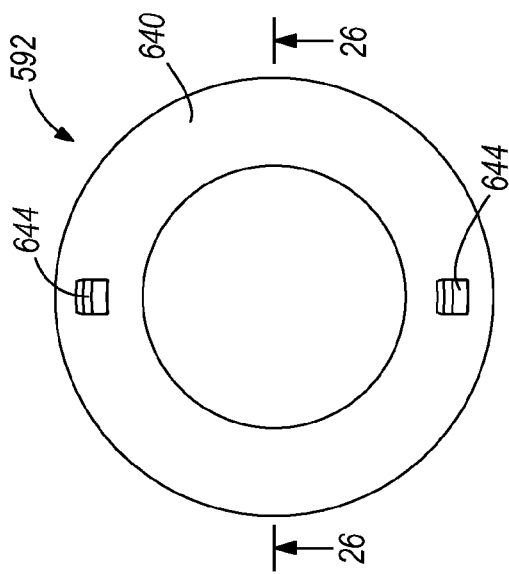
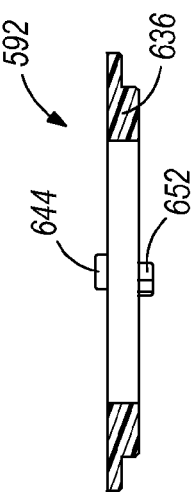
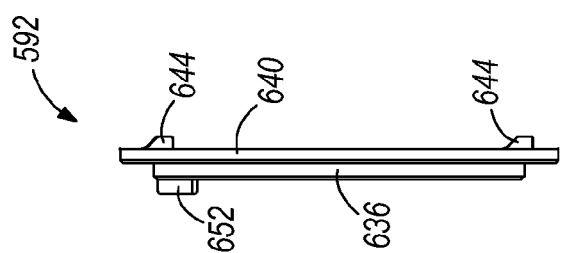

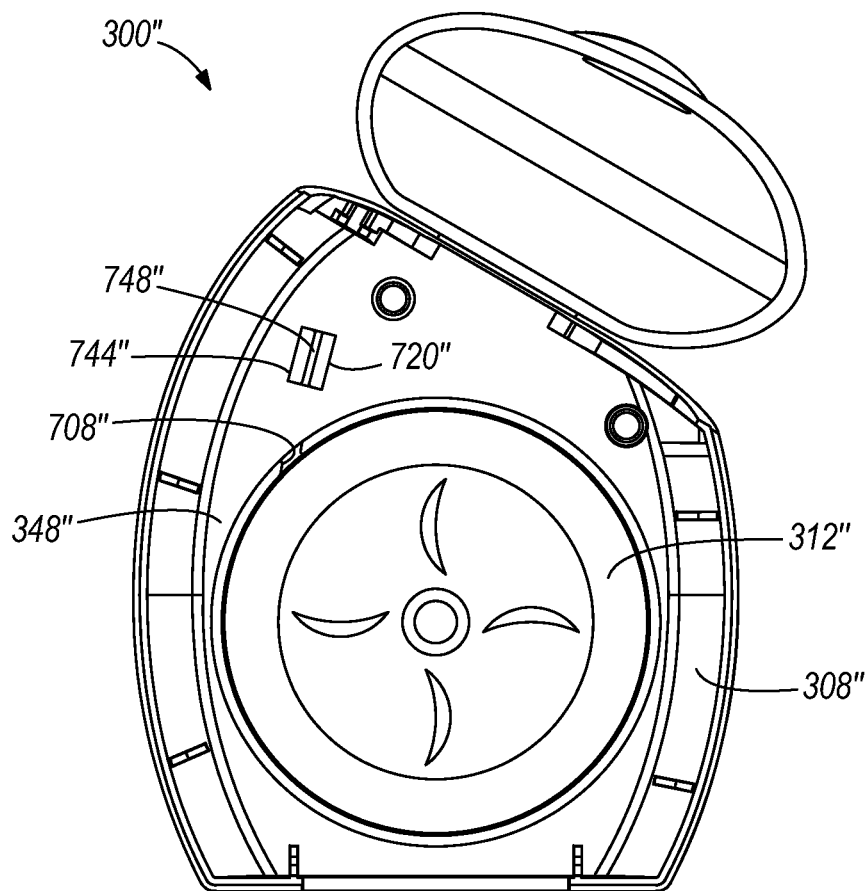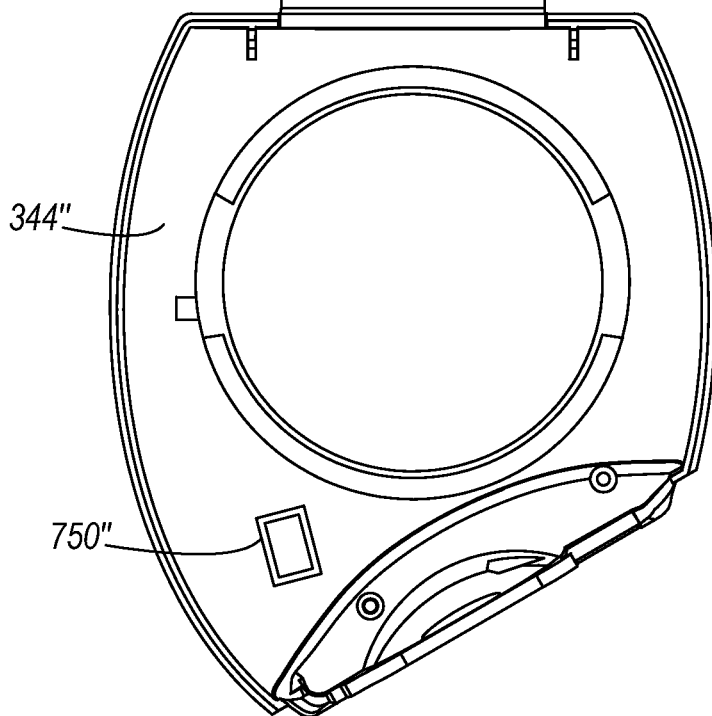
FIG. 50

DISPENSER FOR MULTI-TEXTURE FLOSS

CROSS REFERENCE TO RELATED APPLICATIONS

This application is a continuation-in-part of U.S. patent application Ser. No. 12/975,151, filed Dec. 21, 2010 and published as United States Patent Publication No. 2011/0088717 on Apr. 21, 2011, which in turn is a continuation-in-part of U.S. patent application Ser. No. 12/355,497, filed Jan. 16, 2009 and published as United States Patent Application Publication No. 2009/0194134 on Aug. 6, 2009, which claims the benefit of and priority to U.S. Provisional Patent Application No. 61/024,955 filed Jan. 31, 2008. The entire contents of each of these applications and publications are hereby incorporated by reference.

BACKGROUND OF THE INVENTION

The present invention relates generally to dental floss, and more specifically to dental floss comprising segments having different textures.

Advancements in materials and manufacturing techniques have resulted in a wide range of options when it comes to dental floss. For example, until fairly recently, dental floss options consisted primarily of waxed or unwaxed floss available in various flavors. Currently however, a wide variety of flosses are available, with each variety having its own benefits and limitations. Examples of different materials from which dental floss is currently made include nylon, Polytetrafluoroethylene (PTFE) or "Teflon®," ultra-high molecular weight polyethylene (UHMWPE), and polyester, among others.

Another dental floss option relates to the texture of the floss. Some flosses, such as those formed of PTFE, are designed to be relatively thin and smooth, which allows them to more easily pass through the space between adjacent teeth. Other flosses are designed to be relatively thick, textured, or coarse to remove plaque and other debris more effectively from the larger spaces between adjacent teeth. While many people appreciate the ease of use associated with a relatively thin and smooth floss, many dentists recommend the thick and coarse floss for more effective cleaning.

SUMMARY

In some embodiments, the invention provides a dental treatment device in the form of a thread or floss, the thread including a plurality of first segments and a plurality of second segments. Each first segment extends a first length and includes a first texture and a first cross-sectional dimension. Each second segment extends between adjacent ones of the first segments for a second length, and include a second texture and a second cross-sectional dimension. The second texture is substantially dissimilar from the first texture, and the second cross-sectional dimension is substantially dissimilar from the first cross-sectional dimension. The thread includes alternating ones of the first and second segments.

In other embodiments, the invention provides a method of making dental floss that includes applying tension to a length of thread to thereby reduce at least one cross-sectional dimension of the length of thread. A portion of the tensioned length of thread is bonded, the tension is released from the length of thread such that the bonded portion of the length of thread maintains the reduced cross-sectional dimension.

In still other embodiments, the invention provides a method of making multi-texture dental floss that includes unwinding a length of thread from a feed spool and feeding the length of thread through first feed rollers. The length of thread is fed from the first feed rollers to first tensioning rollers, and wound about a drum to apply tension to the length of thread. Applying tension to the length of thread reduces at least one cross sectional dimension of the length of thread. A portion of the tensioned length of thread is bonded by applying an adhesive, which is allowed at least partially to cure while the thread is wound upon the drum. The tension is released from the length of thread by unwinding the thread from the drum to second tensioning rollers, and the length of thread is fed from the second tensioning rollers to second feed rollers. The length of thread is also wound onto a take-up spool.

In some embodiments, the invention provides a dental floss dispensing unit, the dispensing unit including a housing and a supply spool coupled to the housing and having a length of floss wound thereabout. The supply spool having a locked position, where the supply spool is fixed with respect to the housing, and an unlocked position, where the supply spool is free to rotate with respect to the housing.

In other embodiments, the invention provides a dental floss dispensing unit, the dispensing unit including a housing and a length of floss in the housing. The length of floss including first portions and second portions, the first portions having a different stiffness than the second portions. The dispensing unit also includes a locking mechanism engaging the floss and changing between a locked configuration and an unlocked configuration depending upon whether the locking mechanism is engaged with one of the first portions or one of the second portions.

In still other embodiments, the invention provides a dental floss dispensing unit, the dispensing unit including a housing and a length of floss in the housing. The length of floss having first portions and second portions of differing stiffness. The floss dispensing unit also includes a locking mechanism engaging the floss and changing from an unlocked configuration to a locked configuration in response to withdrawal of a predetermined length of floss from the housing.

In still other embodiments, the invention provides a dental floss dispensing unit, the dispensing unit including a housing and a supply spool rotatable with respect to the housing and having a length of floss wound thereabout. The dispensing unit also including a locking mechanism for dispensing a predetermined amount of floss from the housing independently of rotation of the supply spool.

In some embodiments, a dental floss dispensing unit includes a housing, a supply spool, and a metering element. The supply spool is coupled to the housing and has a length of floss wound thereabout. The length of floss includes a free end extending from the housing. The metering element is coupled to the housing and operatively engages a portion of the length of floss. The metering element provides resistance against removal of the length of floss from the housing, and a magnitude of the resistance against removal of the length of floss from the housing is dependent upon at least one property of the portion of the length of floss engaging the metering element.

In other embodiments, a dental floss dispensing unit includes a housing, a supply spool, and a metering element. The supply spool is coupled to the housing and has a length of floss wound thereabout. The length of floss has a plurality of alternating and distinct first and second floss segments. The metering element engages the length of floss and provides resistance to removal of the length of floss from the housing. A magnitude of the resistance changes as each floss segment moves into engagement with the metering element.

In still other embodiments, a dental floss dispensing unit includes a housing that defines an interior volume and an opening communicating with the volume. A length of dental floss is contained by the volume and has a free end extending through the opening. The length of dental floss includes a plurality of alternating first and second segments. The first segments have a first physical property and the second segments have a second physical property that is different from the first physical property. The housing provides a tactilely detectable indexing as alternating first and second segments are withdrawn from the housing.

In still other embodiments, a dental floss dispensing unit includes a housing defining a volume and a supply spool carried by the housing and positioned within the volume. A length of floss is wound about the supply spool and has a free end extending from the housing. The free end can be pulled to unwind floss from the supply spool, and without manipulating the housing the supply spool is manually rotatable to rewind floss onto the supply spool.

BRIEF DESCRIPTION OF THE DRAWINGS

FIG. 3 is a schematic view of a method for manufacturing the multi-texture dental floss of FIG. 1.

FIG. 4 is a schematic view of an alternate method of manufacturing the multi-texture dental floss of FIG. 1.

FIGS. 8a-e illustrate an alternate construction of a dispenser for the multi-texture dental floss of FIG. 1.

FIG. 9 is a section view take along line 9-9 in FIG. 8a.

FIGS. 10a-10b illustrate a housing of the dispenser of FIG. 8a.

FIG. 11 is a section view taken along line 11-11 of FIG. 10a.

FIG. 12 is a section view taken along line 12-12 of FIG. 10a.

FIG. 13 is a section view taken along line 13-13 of FIG. 10a.

FIGS. 14a-14d illustrate a window panel of the dispenser of FIG. 8a.

FIG. 15 is a section view taken along line 15-15 of FIG. 14a.

FIG. 16 is a section view taken along line 16-16 of FIG. 14a.

FIGS. 17a-17b illustrate a roller of the dispenser of FIG. 8a.

FIG. 18 is a section view taken along line 18-18 of FIG. 17a.

FIGS. 19a-19c illustrate a supply spool of the dispenser of FIG. 8a.

FIG. 20 is a section view taken along line 20-20 of FIG. 19a.

FIGS. 22a-22d illustrate a carriage of the dispenser of FIG. 8a.

FIG. 23 is a section view taken along line 23-23 of FIG. 22a.

FIG. 24 is a section view taken along line 24-24 of FIG. 22a.

FIGS. 25a-25d illustrate a disk of the dispenser of FIG. 8a.

FIG. 26 is a section view taken along line 26-26 of FIG. 25a.

FIGS. 29a-29e illustrate a reset button of the dispenser of FIG. 8a.

FIG. 50 illustrates the dispenser of FIG. 49 with the housing in an open position.

Figure 1:
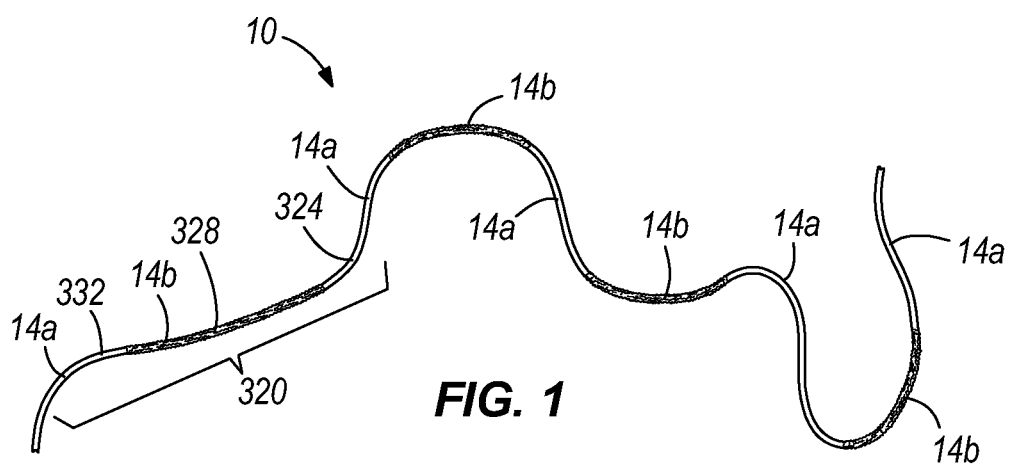
FIG. 1 illustrates a length of multi-texture dental floss embodying the invention.

Before at least one embodiment of the invention is explained in detail, it is to be understood that the invention is not limited in its application to the details of construction and the arrangements of the components set forth in the following description or illustrated in the drawings. The invention is capable of other embodiments and of being practiced or being carried out in various ways.

DETAILED DESCRIPTION

FIG. 1 illustrates a length of multi-texture dental floss 10 embodying the invention. The floss 10 is comprised of alternating segments of floss 14a and 14b having different textures. In the illustrated embodiment, the segments 14a are relatively smooth, while the segments 14b are textured. The segments 14a are configured to more easily fit into the spaces between teeth, while the segments 14b are configured to more effectively remove plaque and debris from the spaces between teeth. The length of floss 10 illustrated in FIG. 1 represents only a portion of a larger length of floss that may be wound onto a spool for storage and dispensing, as discussed further below.

Figure 2:
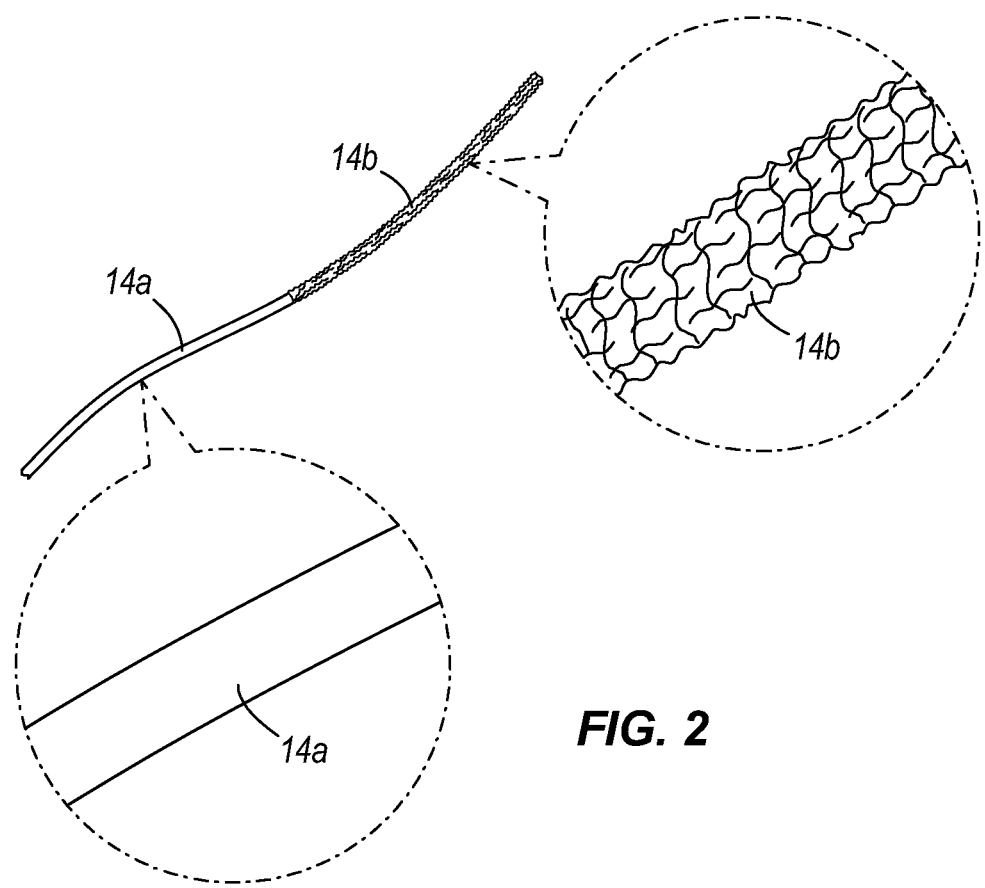
FIG. 2 is an enlarged view of portions of the multi-texture dental floss of FIG. 1.

With reference also to FIG. 2, in some embodiments, the segments 14a may have a thickness in at least one direction that is less than a thickness of the textured segments 14b. For example, the segment 14a may have a thickness in at least one direction of approximately 0.5 mm or less, while the segment 14b may have a thickness in at least one direction of approximately 1 mm or more. In some instances, the segment 14a will have a thickness less than the segment 14b in only one direction. For example, the segment 14a may be formed substantially as a ribbon, having one relatively small cross-sectional dimension, and another relatively large cross-sectional dimension. In such cases, the larger cross-sectional dimension may be substantially equal to a cross-sectional dimension of the segment 14b.

The segment 14b may also be formed substantially as a ribbon but will generally include a minimum cross-sectional dimension that is larger than the minimum cross-sectional dimension of the segment 14a. Furthermore, while the segment 14a is generally provided with a smooth surface texture to ease manipulation of the floss into the space between teeth, the segment 14b is generally provided with a textured surface to more effectively remove plaque and other debris from the space between the teeth. The textured surface may be a result of tightly weaving floss fibers in a way that provides peaks and valleys within the floss, or may be the result of a relatively loose weave that provides a generally circular cross section defined by relatively soft and compliant fibers. Generally speaking, the segments 14a have in common a certain property that distinguishes the segments 14a from the segments 14b, which also have a certain property in common. For example, the segment 14a may be fabricated in a manner that results in the segment 14a being more stiff than the segment 14b. In this regard, the end of a segment 14a can be used to thread a length of floss 10 "end first" into an interdental space, rather than manipulating a central portion of the floss upwardly or downwardly into the space between adjacent teeth. This feature may be particularly helpful for individuals with dental appliances or braces because it allows the floss to be inserted between the dental appliance or braces and the gum line.

FIG. 3 schematically illustrates a first method for making the above-described multi-texture floss 10. The method includes applying tension to a length of floss 22 and winding the taught length of floss 22 around a drum 26. Applying tension to the floss 22 reduces the cross-sectional area and corresponding cross-sectional dimensions of the floss 22. The tension also draws individual floss fibers more closely together, thereby smoothing peaks and valleys that may be present in, for example, a woven floss.

More specifically, the method utilizes a feed spool 23 wound with a supply of uncoated or otherwise untreated floss fiber. The length of floss 22 is uncoiled from the feed spool 23 by a pair of feed rollers 24. The feed rollers 24 then position the floss 22 to be received by first tensioning rollers 25. The first tensioning rollers 25 are preferably rotated by a driving device (e.g. motor, not shown) and direct the length of floss 22 onto the drum 26. The speed of the first tensioning rollers 25 is adjusted so that the length of floss 22 is pulled taught and brought under tension as it is wound onto the drum 26.

The drum 26 is selected to have a circumference that is substantially equal to the desired length of floss that will include at least one smooth segment 14a and at least one textured segment 14b of the finished multi-texture floss 10. After a suitable length of taut floss 22 has been wound around the drum, an adhesive is applied to a section 30 of the drum 26 and thus to the floss 22 by rolling, spraying, or otherwise applying the adhesive in an axial direction from one end of the drum 26 to the other. One example of a suitable adhesive includes cyanoacrylate, however other adhesives may also be used. In some embodiments, the adhesive is applied to the drum 26 and floss 22 in an approximately one to two inch wide strip. In the illustrated construction, the section 30 includes an axially-extending channel into which the adhesive may be sprayed. By spraying the adhesive into a channel the adhesive can be applied uniformly about the exposed outer surfaces of the length of floss 22.

After the adhesive has set, the floss 22 is unwound from the drum 26. The floss 22 then passes through second tension rollers 27. The second tension rollers 27 are preferably rotated by a driving device (e.g., motor, not shown) at an adjustable speed to maintain the tension in the floss 22. After passing through the second tension rollers 27, the tension that was previously applied to the floss to reduce its cross-sectional area is relieved and the sections of floss that did not receive adhesive return to their original size, shape, and texture. These sections become the textured sections 14b of the finished multi-texture floss 10. However, the portions of the floss 22 to which the adhesive was applied maintain the reduced cross-sectional area and reduced cross-sectional dimensions provided by applying tension to the floss, and the surface of the floss is more uniform than before processing as a result of the bonding and smoothing properties provided by the adhesive. These portions become the smooth segment 14a of the finished multi-texture floss 10. The floss 22 then passes through feed rollers 28 that position the floss 22 for coiling on a take-up spool 29. The take-up spool 29 is generally cylindrical and includes an outer diameter 31. The outer diameter 31 is selected to be relatively large so that as the floss 22 continues to cure, it takes on a more linear configuration.

In some embodiments, as the finished floss 10 is unwound from the take-up spool 29, it may be coated under light tension on standard coating equipment in a second manufacturing operation. Such coatings may include paraffin wax, vinapas, liquid nylon, polyethylene glycol, flavoring, or coloring. In yet other embodiments, the finished floss 10 may be packaged into spools, such as the spools discussed below, or may be cut to length and packaged as individual strands having at least one each of a smooth segment 14a and a textured segment 14b. In yet another embodiment, the floss may undergo the light tension coating procedure before being wound onto the take-up spool 29 as an additional step of the multi-texturing process.

It should be appreciated that instead of applying a single strip of adhesive to the floss 22 wound upon the drum 26, multiple strips of adhesive could also be applied, resulting in multiple smooth and textured segments 14a, 14b for each individual winding of floss 22. In this regard, the circumference of the drum 26 and the number of adhesive applications may be selected to meet the demands of a particular manufacturing process.

FIG. 4 illustrates another method for making the above-described multi-texture floss 10 including the use of sonic welding. In this method, a length 22a of uncoated or otherwise untreated floss is unwound from a feed spool 23a. The floss is then fed through first feed rollers 24a and first tension rollers 25a similar to the uncoiling and feeding steps described above. In the embodiment of FIG. 4, the first tension rollers 25a cooperate with second tension rollers 27a such that the floss extending between the first and second tension rollers 25a, 27a is under tension, thereby reducing its cross-sectional area and cross-sectional dimensions as described above. The tensioned length of floss 22a is advanced between first and second dies 50a, b of a sonic welding device 52. The first and second dies 50a, b are closed and the portion of the floss between the dies is sonically welded. The sonic welding bonds the floss fibers together such that, once tension on the floss is removed by advancing the floss past the second tension rollers 27a, the sonically welded portion of floss maintains its reduced cross-sectional area and reduced cross-sectional dimensions. The sonically welded portion of floss thereafter form a smooth segment 14a of the finished multi-texture floss 10, and the untreated portions of floss on either side of the sonically welded portion of floss become textured segments 14b of the finished multi-texture floss 10. The length of the smooth segment 14a will substantially correspond to the size of the dies 50a, b. In some embodiments, the smooth segments 14a have a length of between about one and two inches.

After forming one smooth segment 14a, the length of floss is advanced to position a new portion of floss between the dies of the sonic welding device. The length of the textured segments 14b can be adjusted by advancing the floss by varying amounts through the rollers 25a, 27a between welding operations. As with the method described above, the floss 22 passes through a pair of feed rollers 28a that position the floss 22a for coiling on a take-up spool 29a. The take-up spool 29a is generally cylindrical and includes an outer diameter 31a. The floss 22a may similarly be coated under light tension on standard coating equipment in a second manufacturing operation. Such coatings may include paraffin wax, minapause, flavoring, and/or coloring. In yet other embodiments, the finished floss 10 may be packaged into spools, such as the spools discussed below, or may be cut to length and packaged as individual strands having at least one each of a smooth segment 14a and a textured segment 14b. In yet another embodiment, the floss may undergo the light tension coating procedure before being wound onto the take-up spool 29a as an additional step of the multi-texturing process.

Examples of known flosses that may be manufactured using the methods described above to create the multi-textured floss 10 include GUM® brand Butler Weave® floss, GUM® brand Expanding Floss, GUM® brand Eez-Thru® floss, and GUM® brand waxed or unwaxed flosses. These and other suitable flosses may be made from one or more materials such as nylon, polytetrafluoroethylene (PTFE), ultra-high molecular weight polyethylene (UHMWPE), and polyester, among others.

For example, GUM® brand Butler Weave® floss is a braided nylon dental floss of approximately 840 denier that may be waxed or unwaxed. GUM® brand Expanding Floss is a twisted waxed nylon dental floss of approximately 700 denier that, when untreated, expands when abraded or upon contact with moisture during use. When treated to create multi-texture floss 10 using one of the methods described above, only the textured segment 40 of the Expanding Floss will expand during use. GUM® brand Eez-Thru® floss is a monofilament of polytetrafluoroethylene (PTFE) of between about 810 and 990 denier. GUM® brand waxed or unwaxed flosses are formed of twisted, shred resistant fine nylon of approximately 700 denier.

Figure 5:
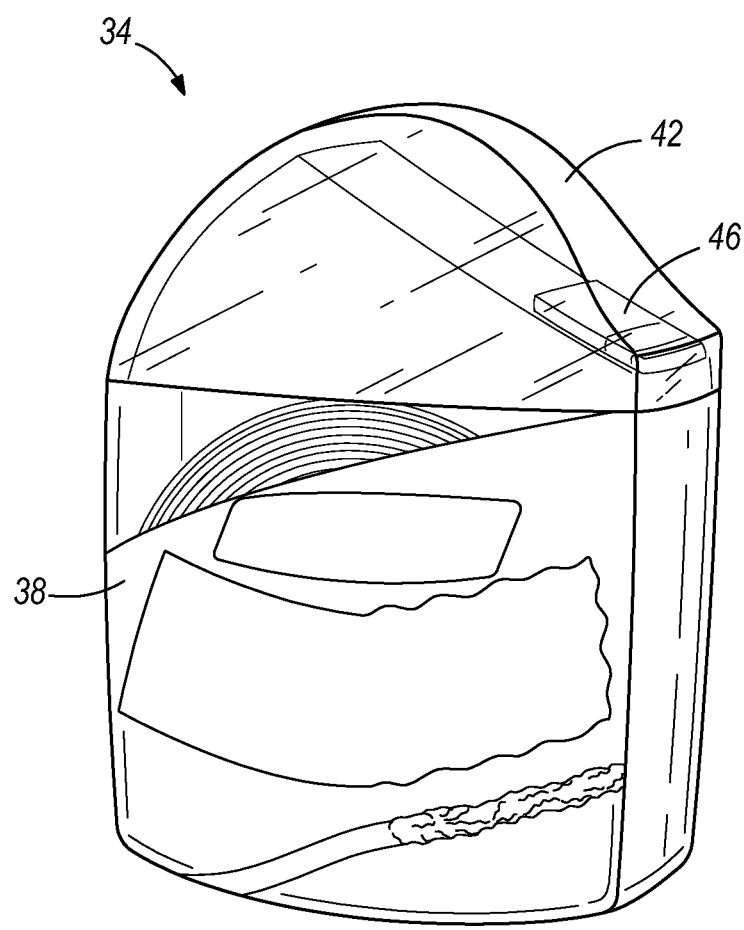
FIG. 5 is a perspective view of a dispenser for the multi-texture dental floss of FIG. 1.

FIG. 5 illustrates a dispenser 34 for the multi-texture floss 10. While various configurations are possible, the illustrated dispenser 34 includes a body 38 and a cover 42. The body 38 rotatably supports a spool (not shown) upon which a length of floss 10 having a plurality of segments 14a, 14b is wound. Because the smooth segments 14a tend to retain the shape of the spool onto which they are wound, the spool preferably has a diameter that is greater than the diameter of traditional dental floss spools. In this way, the curvature of the smooth segments 14a once removed from the spool is reduced.

The body 38 also defines an opening 46 through which the floss 10 can be dispensed. The opening 46 may include, among other things, a reduced aperture, a flap portion biased against the floss, or a detent arrangement to provide a tactilely detectable indexing of the floss as the alternating smooth segments 14a and textured segments 14b are withdrawn from the body 38 and pass through the opening 46. Floss cutting and floss retention tabs (not shown) may also be provided on the body 38, or the floss may be severed and retained by structure provided on the cover 42 when the cover 42 is closed against the body 38.

Figure 6:
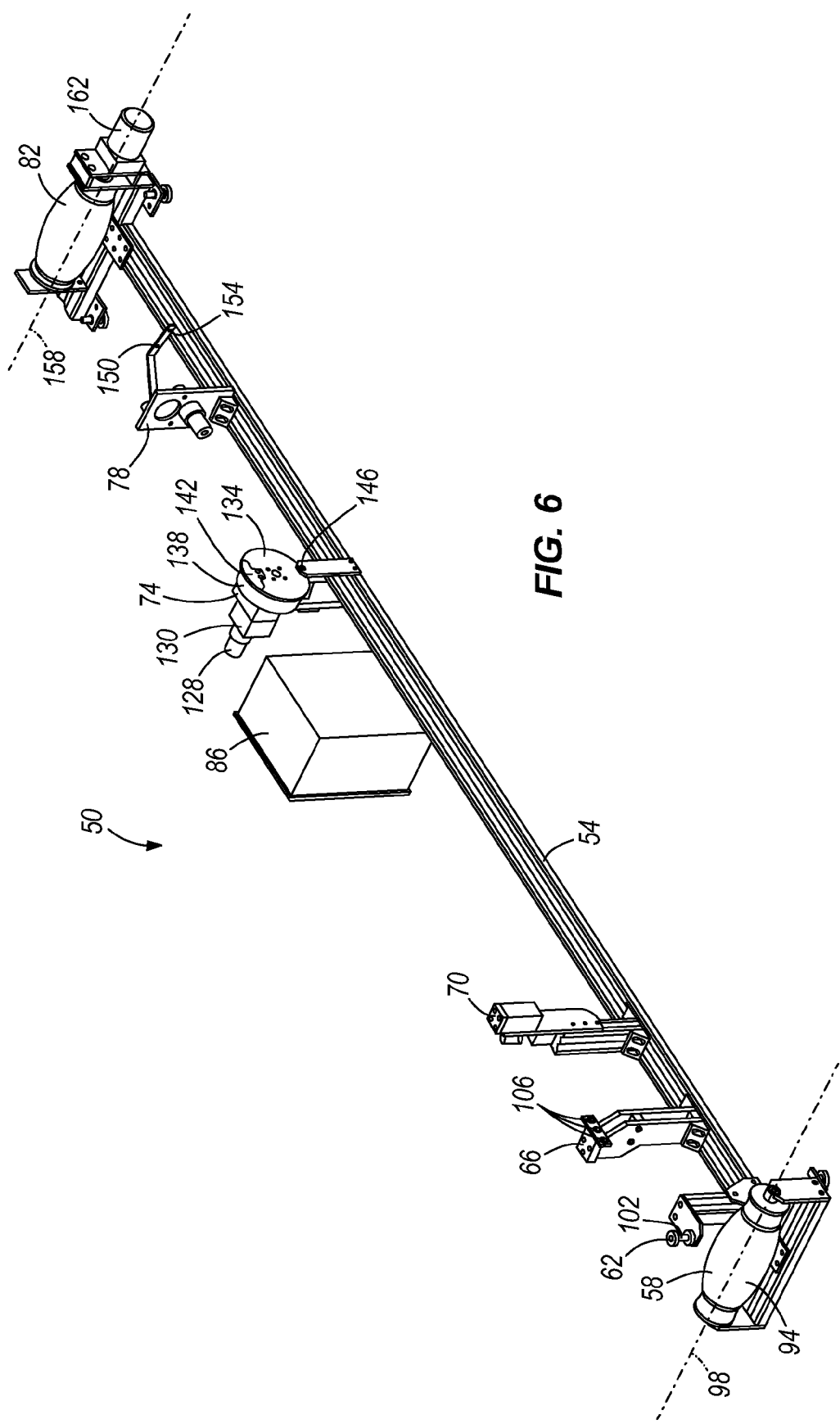
FIG. 6 is a perspective view of a manufacturing assembly for manufacturing a multi-texture dental floss.
Figure 7:
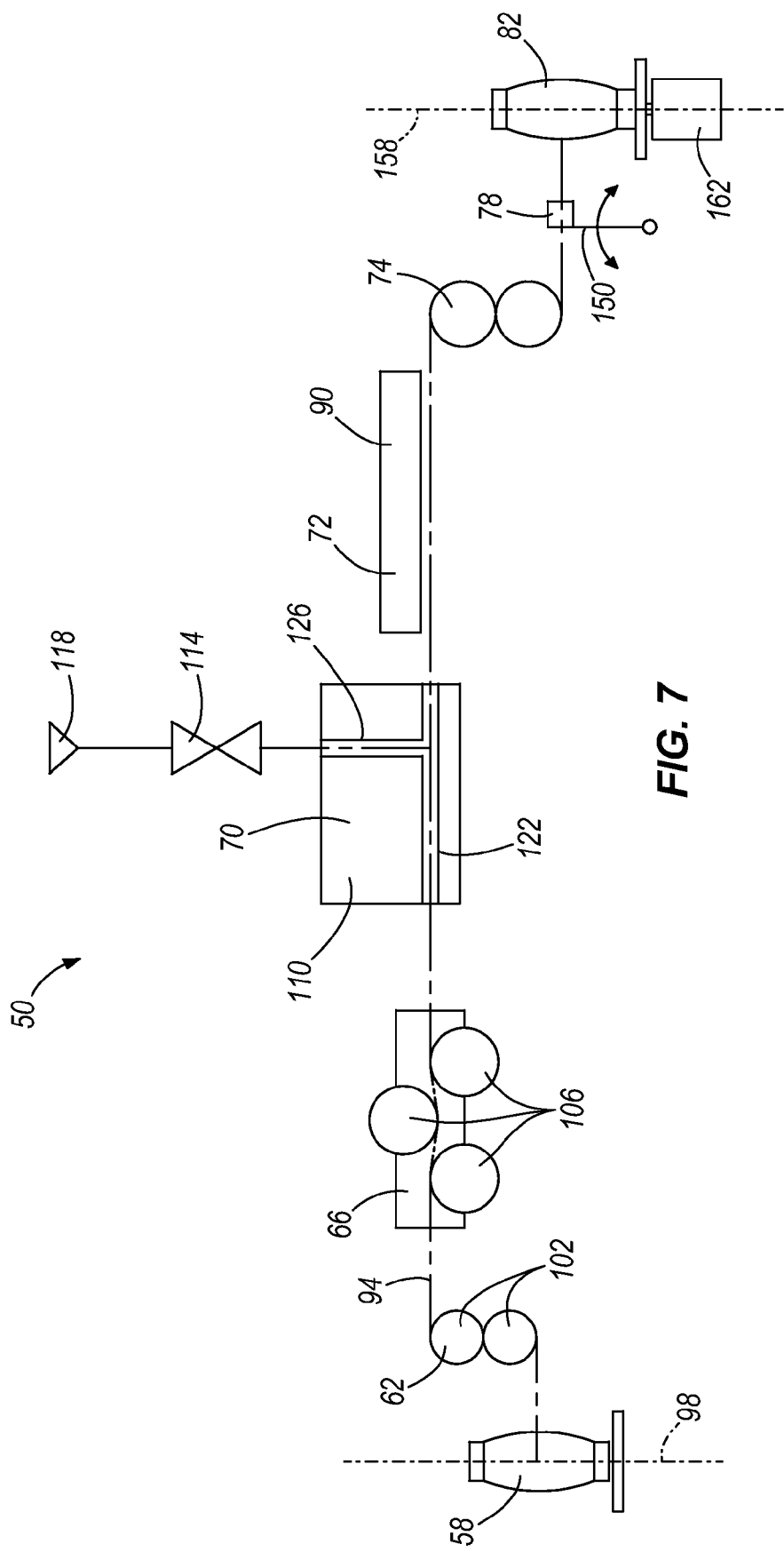
FIG. 7 is a schematic diagram of the manufacturing assembly of FIG. 6.

FIG. 6 illustrates a manufacturing assembly 50 capable of performing yet another method for manufacturing multi-texture floss, such as the multi-texture floss 10. FIG. 7 is a schematic diagram depicting certain components of the manufacturing assembly 50. The manufacturing assembly 50 includes a spine or frame 54 to which the various components of the assembly 50 are coupled. The frame 54 may be fabricated from any suitable material, such as various steel or aluminum alloys, and in some embodiments may be formed from commercially-available channel track that allows for rapid mounting and adjustment of the components along the frame 54. In other embodiments, the components may be mounted to individual frames or other structures.

Moving from left to right in FIGS. 6 and 7, the assembly 50 includes an unwind spool 58, a tensioning device 62, a tension transducer 66, an adhesive dispensing assembly 70, a curing section 72, a drive assembly 74, a spooling dancer arm 78, and a wind up spool 82. In the illustrated embodiment, the unwind spool 58, tensioning device 62, tension transducer 66, adhesive dispensing assembly 70, drive assembly 74, spooling dancer arm 78, and wind up spool 82 are each mounted to the frame 54. The assembly 50 also includes a control assembly 86 (FIG. 6) that may or may not be mounted to the frame 54. In some embodiments, the curing section 72 may include an optional curing station 90 (FIG. 7) for curing certain compounds that may be applied to the floss.

The unwind spool 58 carries a bulk quantity of floss 94 that typically but not necessarily is a substantially uniform, single-texture floss. For example, the floss 94 carried on the unwind spool 58 may be or include one or more of the specific floss types or brands identified above. The unwind spool 58 is mounted for rotation about an axis 98. In the illustrated embodiment the axis 98 is horizontal, but in other embodiments the axis 98 may be vertical (e.g., similar to a turn table), or at an angle between horizontal and vertical. The unwind spool 58 can be mounted upon any suitable supports, and may include a tensioning mechanism (not shown) that resists slightly the unwinding of floss 94 from the unwind spool 58. The tensioning mechanism can be used to prevent the rotational momentum of the unwind spool 58 from continuing to unwind floss when the assembly 50 slows or stops. The unwind spool 58 generally is not driven by its own motor or actuator, but instead rotates to unwind the floss 94 in response to pulling forces applied to the floss 94 by other components of the assembly 50.

As indicated by the dashed line of FIG. 7, the floss 94 unwinds from the unwind spool 58 and extends to and through the tensioning device 62. The tensioning device 62 may take on a variety of forms, but generally includes a cylinder 102 (FIG. 6) or pair of cylinders 102 (FIG. 7) around and/or between which the floss 94 extends. The following description refers to a tensioning device 62 having a single cylinder 102, however the similar principles apply to a tensioning device 62 having two or more cylinders 102. The cylinder 102 is rotatably mounted such that, as the floss is drawn around the cylinder 102, the cylinder 102 rotates. To apply tension to the floss 94, the rotatable mounting of the cylinder 102 does not allow for free or substantially free rotation of the cylinder 102. Rather, cylinder 102 is mounted in a way that provides a controlled resistance to rotation. In some embodiments, the resistance to rotation may be substantially constant. In other embodiments, the resistance to rotation may be adjustable, thereby allowing for adjustments in the amount of tension applied to the floss. In some embodiments with adjustable resistance to rotation, the adjustment may be automatically controllable by way of the control assembly 86, as described further below. The tensioning device 62 applies tension to the floss 94 such that, as discussed above, at least one cross sectional dimension of the floss 94 is reduced. Generally speaking, the greater the tension on the floss 94, the greater the reduction in the at least one cross sectional dimension.

After passing through the tensioning device 62, the floss 94 passes through the tension transducer 66. In the illustrated embodiment, the tension transducer 66 includes three spaced-apart rollers 106 that together define a serpentine path along which the floss 94 extends. The tension transducer 66 includes a suitable sensor, such as one or more strain gauges or other displacement sensor(s) (not shown), that measures the displacement of the middle roller due to the floss 94 extending along the serpentine path between the rollers 106. The higher the tension on the floss 94, the greater the displacement of the middle roller 106. As the use of strain gauges suggests, the displacement of the middle roller 106 may be extremely small. Signals from the sensor may be processed internally by the tension transducer 66 and communicated to the control assembly 86, or unprocessed or "raw" signals from the sensor(s) within the tension transducer 66 may be communicated directly to the control assembly 86, and the control assembly 86 may then perform suitable signal processing. In either case, signals corresponding the amount of tension in the floss 94 are communicated to the control assembly 86 so suitable adjustments may be made by an operator or by the control assembly 86 itself. In one exemplary embodiment, the tension in the floss 94 is maintained between about 100 and 400 grams.

After passing through the tension transducer 66, the floss 94, while remaining under tension, passes through the adhesive dispensing assembly 70. In the illustrated embodiment, the adhesive dispensing assembly 70 includes a coating die 110, a control valve 114 that regulates the supply of adhesive to the coating die 110, and an adhesive supply 118. With reference primarily to FIG. 7, the coating die 110 includes a floss passageway 122 through which the floss 94 extends, and a supply passageway 126 that intersects the floss passageway 122 and delivers adhesive to the floss passageway 122. The supply passageway 126 also communicates with the control valve 114, which operates to intermittently supply adhesive to the supply passageway 126 and the floss passageway 122 for application of adhesive to the floss. The control valve 114 receives adhesive from the adhesive supply 118. As the floss 94 passes through the floss passageway 122 portions of the floss collect, e.g., are coated with, the adhesive that is intermittently supplied to the floss passageway 122 by way of the supply passageway 126 and the control valve 114.

The adhesive supply 118 may be or include, without limitation, a bulk volume of adhesive, such as an elevated storage tank, a pressurized line containing adhesive, or any combination of these or other suitable volumes and/or conduits for supplying adhesive to the control valve 114 and coating die 110. The control valve 114 may be or include a solenoid operated valve or other suitable valve that is capable of controlled, intermittent operation between on and off positions. As discussed further below, the control valve 114 operates to intermittently supply adhesive to the supply passageway 126 and the floss passageway 122 such that, as the floss 94 is drawn through the floss passageway 122, adhesive is intermittently applied to spaced-apart segments of the floss 94. In this way, some segments of floss receive adhesive, and other segments of floss do not receive adhesive. With reference also to FIGS. 1 and 2, the segments of floss that receive adhesive while passing through the adhesive dispensing assembly 70 correspond to the relatively smooth segments of floss 14a, while the segments of floss that do not receive adhesive while passing through the adhesive dispensing assembly 70 correspond to the textured segments 14b of floss 10.

After passing through the adhesive dispensing assembly 70, the floss 94 travels along a curing section 72 for curing of the adhesive that has been applied to segments of the floss 94. As shown in FIG. 6, the curing section 72 extends between the adhesive dispensing assembly 70 and the drive assembly 74, and comprises a relatively large portion of the overall length of the assembly 50. For example, in the exemplary embodiment of FIG. 6, the curing section 72 is longer than the distance between the unwind spool 58 and the adhesive dispensing assembly 70. The extended length of the curing section 72 allows the adhesive applied to the floss 94 by the adhesive dispensing assembly 70 to cure before the floss 94 arrives at the drive assembly 74.

A variety of suitable adhesives or combinations of adhesives may be applied by the adhesive dispensing assembly 70 or, in some embodiments, by two or more adhesive dispensing assemblies 70 (e.g., for application of multi-part adhesives). For example, the embodiment of FIG. 6 uses an air cure cyanoacrylate that cures sufficiently in the time it takes the floss to travel from the adhesive dispensing assembly 70 to the drive assembly 74. Other embodiments may utilize adhesives that are cured by way of exposure to certain types of light (e.g., UV light), heat, or other environments, without limitation. Such embodiments may include the optional curing station 90 illustrated in FIG. 7. The optional curing station 90 may be or include lights, heating elements, or other devices that expose the adhesive to whatever environment is necessary to cure the adhesive.

After passing through the curing section 72 the floss 94 arrives at the drive assembly 74. In the illustrated embodiments, the drive assembly 74 is a variable speed drive assembly, the speed of which can be controlled by the control assembly 86. The illustrated drive assembly 74 includes a motor 128, which may be electric, hydraulic, pneumatic, or the like, a drive unit 130 coupled to the motor 128, and a drum 134 coupled to the drive unit 130. The motor 128, in combination with the drive unit 130, is operable to rotate the drum 134 at a desired speed. The drum 134 includes an outer cylindrical surface 138 having a circumference that corresponds to a desired length of a single floss fragment, which in the present invention includes the combined length of a single smooth segment of floss 14a and a single textured segment 14b of floss 10 (see FIG. 1).

The floss 94 is wound for one revolution about the outer cylindrical surface 138. Rotation of the drum 134 by the motor 128 and drive unit 130 pulls the floss 94 off of the unwind spool 58 and through the tensioning device 62. As such, the entire length of floss extending between the tensioning device 62 and the drive assembly 74, including the floss extending through the tension transducer 66 and the adhesive dispensing assembly 70, is under tension, thereby reducing at least one cross sectional dimension of the floss 94, as discussed above. After the floss 94 travels around the drum 134, the tension on the floss 94 is reduced or eliminated, thereby allowing the segments of floss that did not receive an application of adhesive to relax, which results in an increase of the at least one cross sectional dimension of the floss 94 for those segments.

In the illustrated embodiment, the drum 134 also functions as an encoder wheel that regulates the operation of the adhesive dispensing assembly 70. As shown in FIG. 6, an arcuate sensor plate 142 is coupled to a side surface of the drum 134 for rotation therewith, and a sensor 146 is positioned adjacent the side surface and along the outer circumference of the drum 134, but is fixed relative to the frame 54. The sensor 146 is operable to sense the presence or absence of the sensor plate 142 as the drum 134 rotates, and communicates with the control assembly 86. The control assembly 86, in turn, operates the control valve 114 of the adhesive dispensing assembly 70 in response to signals received from the sensor 146. Specifically, in the illustrated embodiments when the sensor plate 142 is not positioned in front of the sensor 146, the control assembly 86 turns the control valve 114 off such that adhesive is not applied to the floss 94. When the sensor plate 142 is positioned in front of the sensor 146, the control assembly 86 turns the control valve 114 on such that adhesive is applied to the floss 94. In some constructions, multiple drive assemblies 74, each controlling an individual adhesive dispensing assembly, may be present.

The sensor plate 142 has an arc length approximately equal to the desired length of a single smooth segment of floss 14a. In the illustrated construction, this arc length is about one-fourth of the total circumference of the drum. As discussed above, the circumference of the drum 134 corresponds to the desired combined length of a single smooth segment of floss 14a and a single textured segment 14b of floss 10 (e.g., a floss fragment). Thus, in the illustrated embodiment, the length of a smooth segment of floss 14a (e.g., floss to which adhesive has been applied while the floss is under tension) will be equal to about one-third of the total length of a textured segment 14b of floss 10 (e.g., floss to which no adhesive has been applied). Of course, the relative lengths of the smooth segment 14a and textured segment 14b of floss may vary depending upon the desired configuration of the finished floss 94.

Since the drum 134 doubles as both a drive unit and an encoder wheel, the operation of the control valve 114 automatically adjusts in proportion with the speed of the drive unit 130. As such, any change in the speed of the drum 134 results in a proportional change in the frequency and duration that adhesive is applied to the floss 94 as it passes through the adhesive dispensing assembly 70. Therefore the length of the smooth segment 14a and the proportions between the smooth and textured segments (e.g., 1:3) are maintained.

During operation, the size, number, and position of the smooth segments 14a within a given floss fragment can be adjusted by altering the size, quantity, and position of the sensor plates 142 along the circumference of the drum 134. More specifically, increasing the arcuate length of a particular sensor plate 142 will increase the duration that adhesive will be applied to the floss 94, increasing the length of that particular smooth segment 14a. Furthermore, adding, removing, or altering the location of each sensor plate 142 with respect to other sensor plates 142 will modify the number and relative position of each smooth segment of floss 14a in a particular floss fragment. In constructions where more than one sensor plate 142 is present, altering the distance between the two plates 142 can also be used to establish the length of the texture segments 14b.

After passing through the drive assembly 74 the floss 94 arrives at the spooling dancer arm 78. The spooling dancer arm 78 directs the floss 94 onto the wind-up spool 82 as it travels from the drive assembly 74. Illustrated in FIG. 6, the dancer arm 78 includes a motor, actuator, drive screw, or the like (not shown) driving a swing arm 150 that pivots from side to side so the floss 94 winds onto the wind-up spool 82 in a desired pattern (e.g., evenly, tapered, or the like). The swing arm 150 includes an aperture 154 through which the floss 94 passes, allowing the swing arm 150 to determine the axial position along the spool 82 that the floss 94 will be wound.

In alternate constructions, the spooling dancer arm 78 may not pivot but instead traverse along a drive screw or rotate about an axis. In still other constructions, the spooling dancer arm 78 may include a stationary aperture through which the floss 94 passes while the wind-up spool 82 is moved axially to alter the position that the floss 94 will be wound.

After passing through the spooling dancer arm 78, the floss is wound about the wind-up spool 82. The wind-up spool 82 carries the finished floss 94, and may define an outer diameter that is generally greater than that of a standard spool used to store floss to minimize the curvature of the floss as it is removed from the spool 82. The wind-up spool 82 is mounted for rotation about an axis 158. In the illustrated embodiment the axis 158 is horizontal, but in other embodiments the axis 158 may be vertical (e.g., similar to a turn table), or at an angle between horizontal and vertical. The wind-up spool 82 can be mounted upon any suitable supports, and includes a motor 162 to rotate the spool 82. The motor 162 provides the tension in the floss 94 after it has left the drive assembly 74, pulling the floss 94 through the spooling dancer arm 78 and onto the wind-up spool 82 for final storage.

FIGS. 8a-33 illustrate an embodiment of a floss dispenser 300 for dispensing the multi-texture floss 10. The floss dispenser 300 contains a supply of floss 304 (see FIG. 9) and generally controls the amount of floss 10 that can be removed from the dispenser 300 at any one time. The floss dispenser 300 includes a housing 308, a supply spool 312 rotatably supported by the housing 308 and having the floss supply 304 wound thereabout, and a locking mechanism 316 that engages the floss 10 to control the release of floss from the housing 308.

More specifically, the floss dispenser 300 is configured to dispense a single flossing fragment 320 (see FIG. 1) from the housing 308 each time the user operates the dispenser 300. Once a flossing fragment 320 has been removed from the housing 308, the locking mechanism 316 restricts the removal of additional floss 10 from the floss supply 304 (e.g., by preventing rotation of the supply spool 312). Thereafter, the floss dispenser 300 typically remains in a locked configuration until a reset condition is met, such as actuating a reset button, closing a cover, or the like. When the reset condition is met, the locking mechanism 316 returns to its initial configuration and an additional flossing fragment 320 may be removed by the user.

In the present description, a flossing fragment 320 is a length of floss 10 having a certain desired property or properties. The desired properties of the fragment 320 may include, but are not limited to, a particular length, a given number or sequence of segments (e.g., a combination of smooth and textured segments 14a, 14b), a given number or sequence of portions with a particular stiffness, or the like. For purposes of the following description, each flossing fragment 320 includes a leader 324, a center section or body 328, and a tail 332, where the leader and tail 324, 332 are formed by smooth segments 14a of the multi-texture floss 10 and the body 328 is formed by a textured segment 14b of the multi-texture floss 10 (see FIG. 1). This configuration is achieved by cutting each smooth segment 14a such that one portion of the cut smooth segment 14a becomes the leader 324, and the other portion of the cut smooth segment 14a becomes the tail 332.

Illustrated in FIGS. 8a-13, the housing 308 of the floss dispenser 300 includes a substantially flat bottom surface 336 configured to rest on a support surface (e.g., a table top) and curvilinear walls that taper to a rounded point as they extend upwardly from the bottom surface 336 to define a storage volume 340. The housing 308 includes a first or front portion 344, a second or rear portion 348, and a cap portion 352. The housing 308 also includes a window panel 356 coupled to the front portion 344. In the illustrated construction, the front and rear portions 344, 348 are pivotably coupled to one another by a hinge member 360 (see FIG. 10a), such that the portions 344, 348 can be pivoted into and out of engagement with one another during assembly or for replacing the floss supply 304. In the present invention, the portions 344, 348 of the housing 308 are formed as a single piece of material (e.g., molded plastic) however, in alternate constructions, the portions 344, 348 may be formed individually.

Illustrated in FIGS. 10a-11, and 13, the front portion 344 of the housing 308 includes a bottom wall 364, a top wall 368 oriented at an angle to and spaced a distance from the bottom wall 364, and a front wall 372 extending between the top and bottom walls 368, 364. Best illustrated in FIG. 13, the front portion 344 also includes an alignment ridge 384 extending along at least a portion of the periphery 376 of the front portion 344. The alignment ridge 384 provides rigidity to the assembled housing 308 and aligns the front portion 344 with the rear portion 348 during assembly.

The front portion 344 of the housing 308 also includes a plurality of alignment recesses 388b configured to receive alignment pins 388a formed on the rear portion 348. When the front portion 344 and rear portion 348 are joined together, each alignment pin 388a of the rear portion 348 aligns with and is received by a corresponding alignment recess 388b of the front portion 344. The alignment pins 388a and recesses 388b align the front and rear portions 344, 348 of the housing 308 to aid assembly of the floss dispenser 300. In some constructions, the alignment pins 388a and alignment recess 388b are configured for an interference fit, thereby aiding in coupling the two portions 344, 348 to one another. In other constructions, locking tabs, adhesives, or other forms of coupling (not shown) may be used to couple the front portion 344 and the rear portion 348. In still other constructions, alignment pins 388a may be provided on the front portion 344, and alignment recesses 388b may be provided on the rear portion 348.

The bottom wall 364 of the front portion 344 is substantially semi-elliptical in shape, having a curvilinear edge that at least partially defines the contour of the front wall 372. The bottom wall 364 is substantially planar, being configured to rest upon a support surface (e.g., a table top) and maintain the floss dispenser 300 in a substantially vertical orientation. In some constructions, the bottom wall 364 may include feet or be coated in a high friction material (e.g., rubber) to help stabilize the floss dispenser 300 on the support surface.

The top wall 368 of the front portion 344 is generally semi-elliptical in shape and is positioned at an angle with respect to the bottom wall 364. The top wall 368 includes a curvilinear edge that is recessed slightly inwardly from the front wall 372 so the cap portion 352 is flush with the housing 308 when the cap portion 352 is in the closed position (see FIG. 9). The top wall 368 also includes a depression 400, extending into the housing 308, to provide a space for the user's fingers when grasping the floss 10.

Figure 10A:
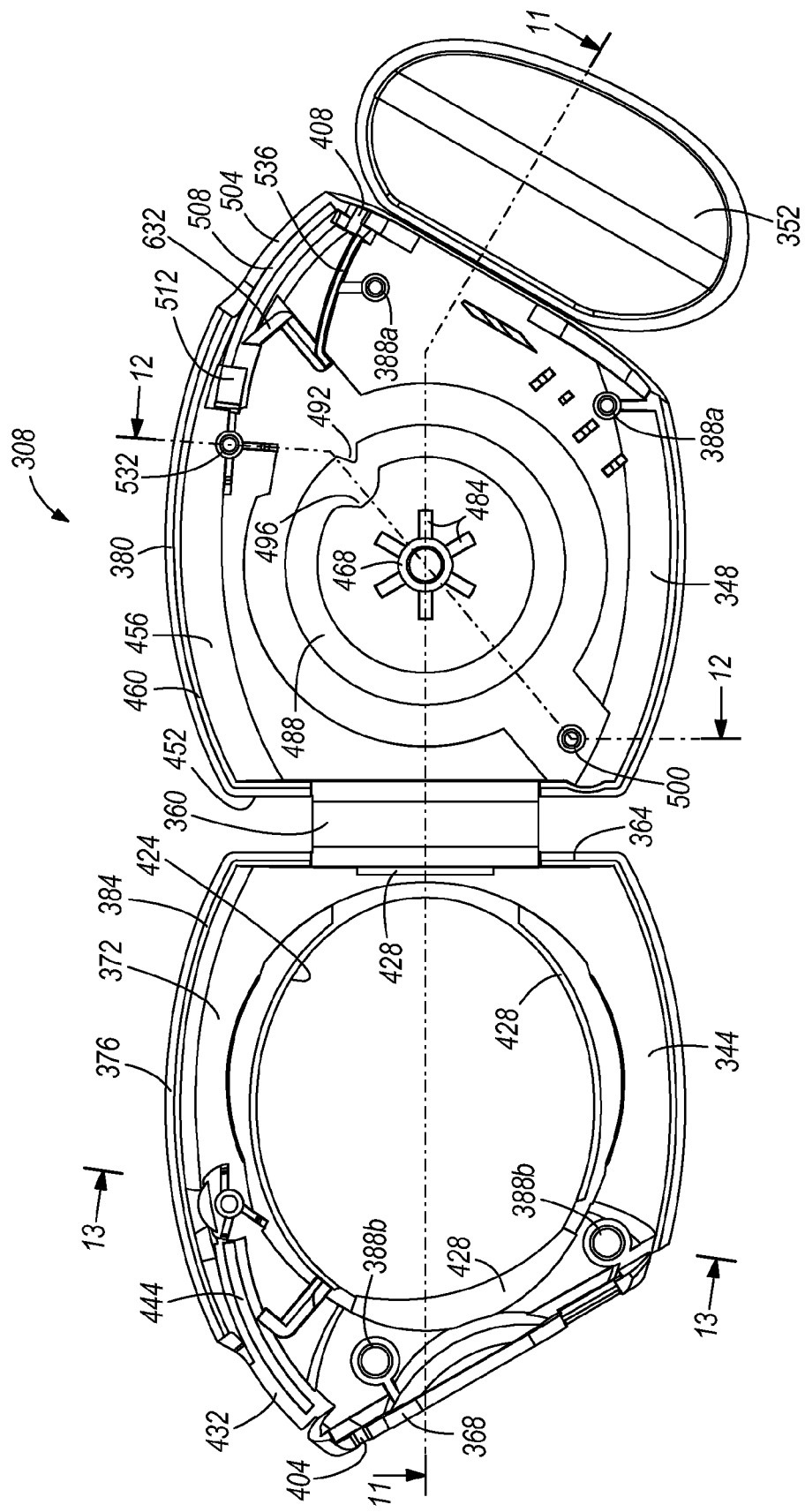
Figure 10B:
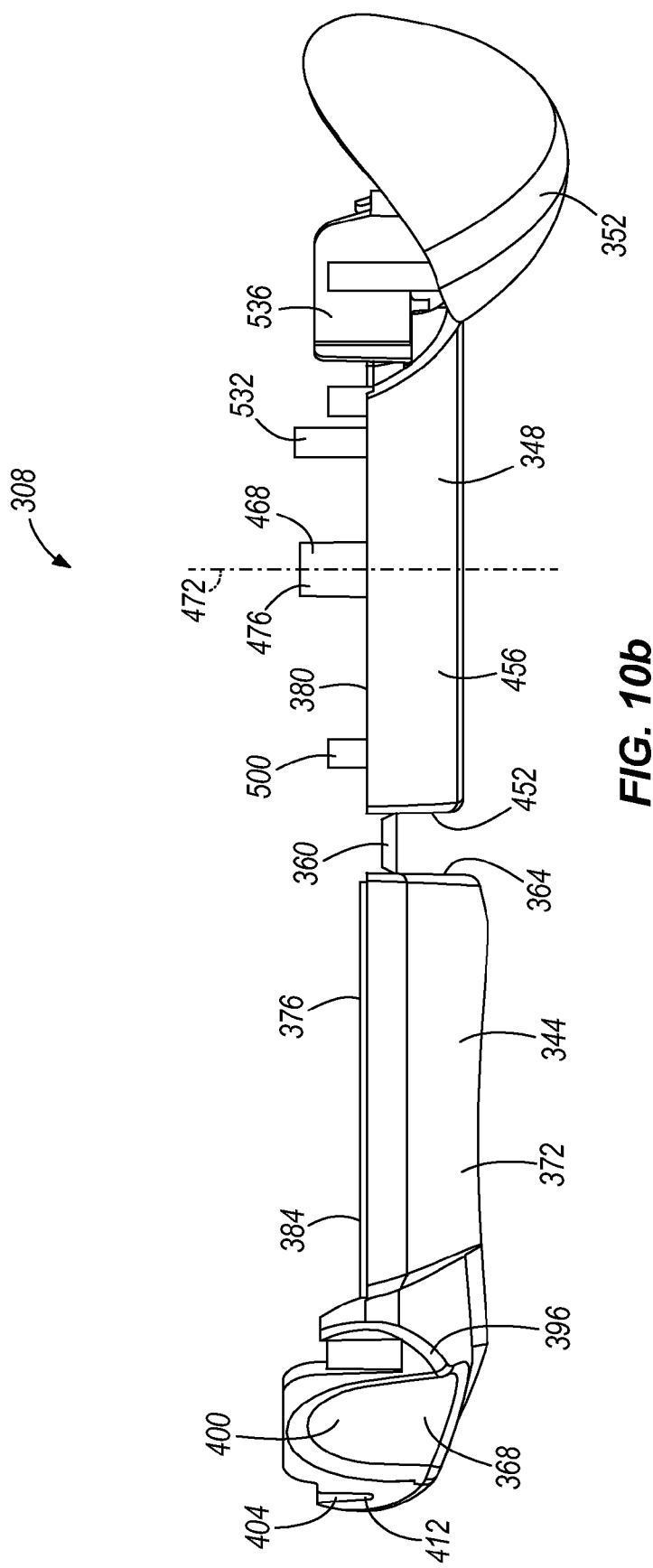

The top wall 368 of the front portion 344 also defines a gradually tapering slot 404 extending inwardly from the periphery 376 (see FIG. 10b). When the housing 308 is assembled, the slot 404 is aligned with and receives a tapered projection 408 that extends from the periphery of the of the rear portion 348 to define an opening 412 through which the floss 10 can be dispensed. In some constructions, the opening 412 may include a resilient flap or other detent arrangement (not shown) to restrict the movement of the floss 10 to a single direction.

Figure 32:
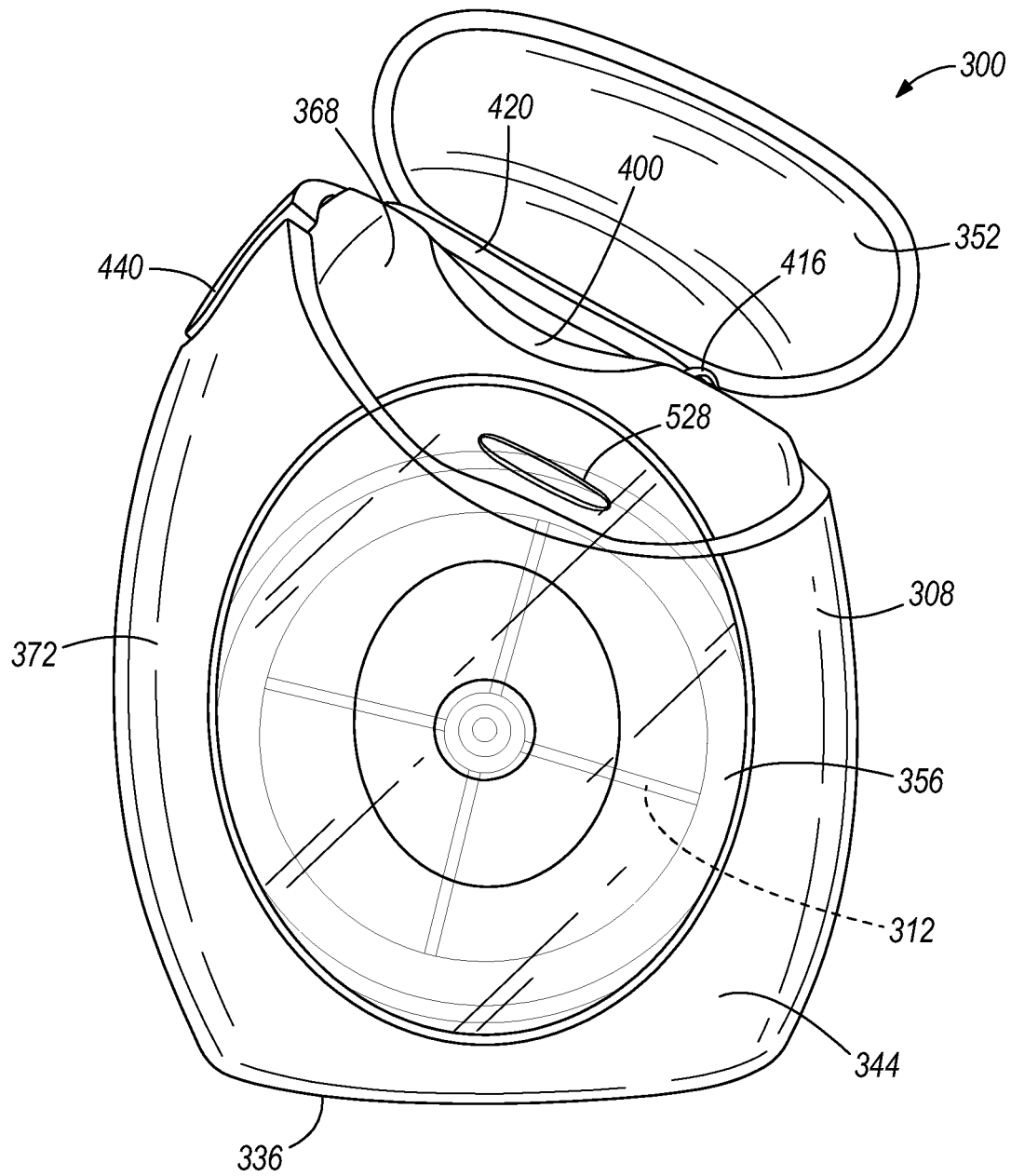
FIG. 32 is a front view of the dispenser of FIG. 8a with the cover portion in an open position.
Figure 33:
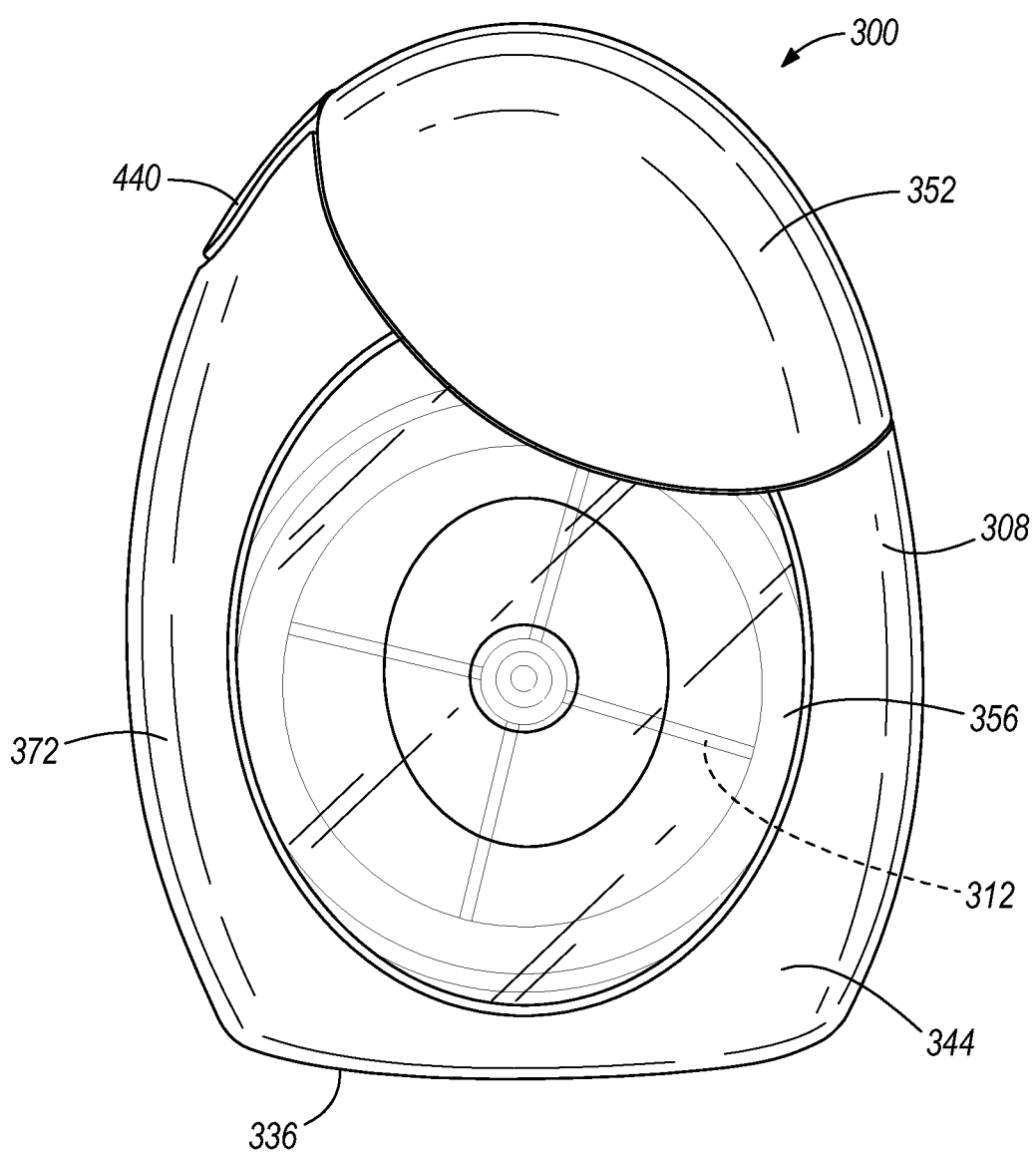
FIG. 33 is a front view of the dispenser of FIG. 8a with the cover portion in a closed position.
Figure 35:
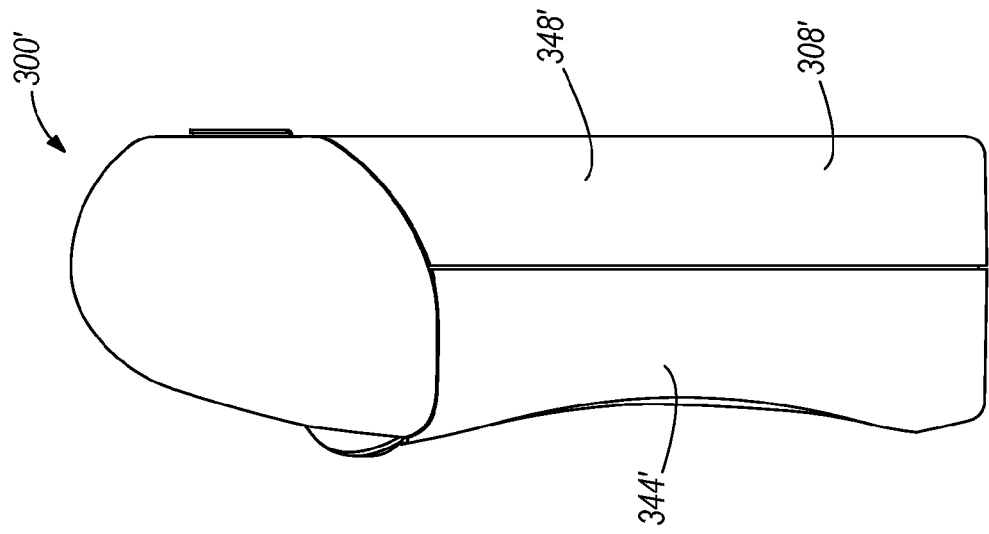
FIGS. 34-38 illustrate an alternate construction of a dispenser for the multi-texture dental floss of FIG. 1.
Figure 34:
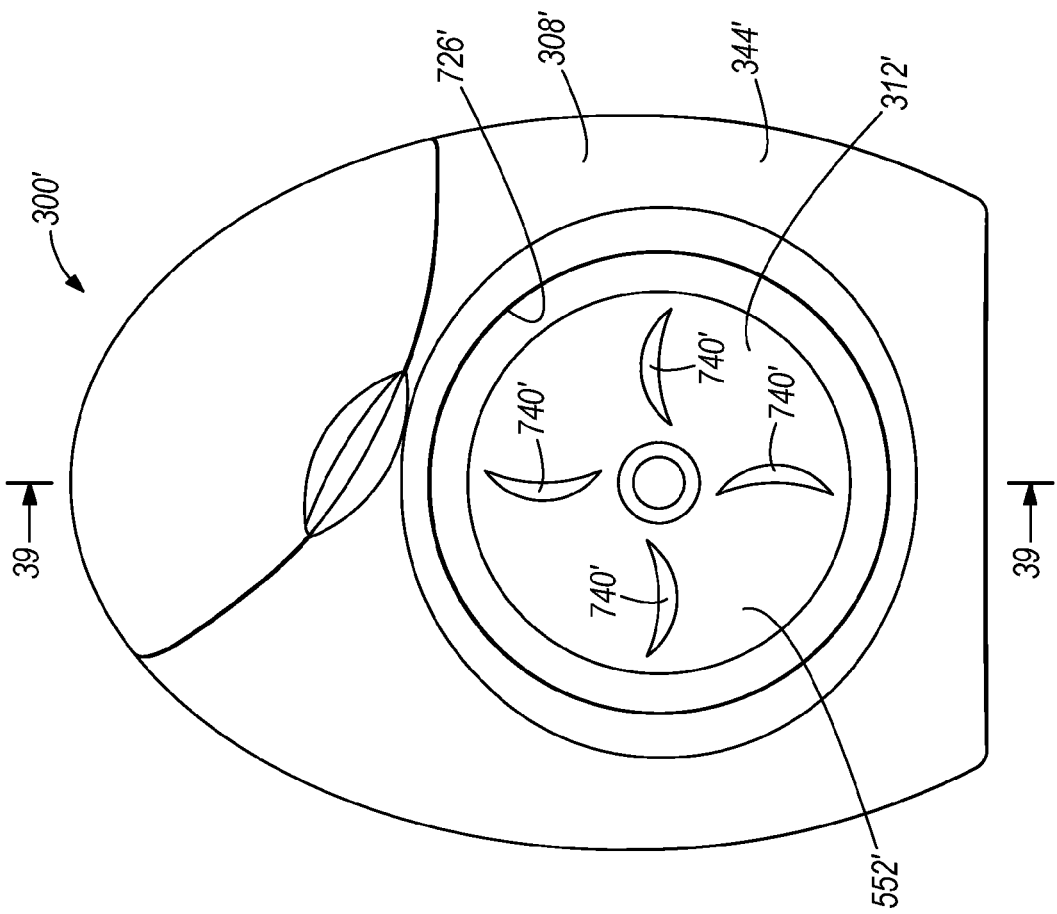
Figure 37:
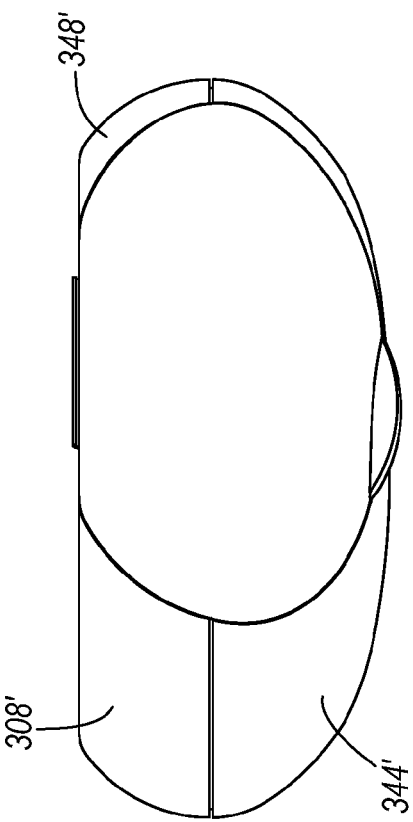
Figure 36:
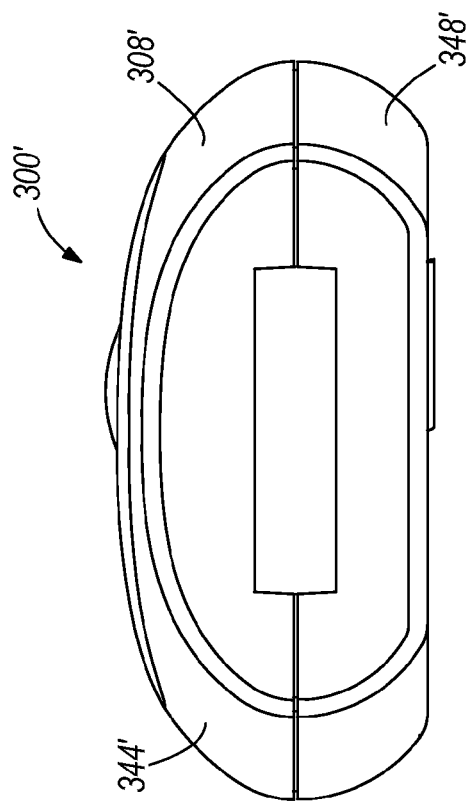

The top wall 368 also includes a cutting member 416 (see FIG. 32). The cutting member 416 is positioned on the top wall 368 opposite the opening 412 with the depression 400 positioned therebetween. The cutting member 416 is configured to sever or cut the dispensed floss fragment 320 from the floss supply 304 so it can be utilized by the user. In the illustrated construction, when the floss fragment 320 is cut from the floss supply 304 end portion 420 of the floss supply 304 is held or pinched within the cutting member 416 where it is held in place for subsequent use.

In the illustrated construction, the cutting member 416 is formed separately from the top wall 368, and may be stamped from a piece of sheet material (e.g., steel). The cutting member 416 includes a C-shaped clip portion able to clasp onto the top wall 368 to position a cutting tab in an appropriate position. In other constructions, the cutting member 416 may be molded into the housing 308 or adhered to the top wall 368 by an adhesive.

Figure 11:
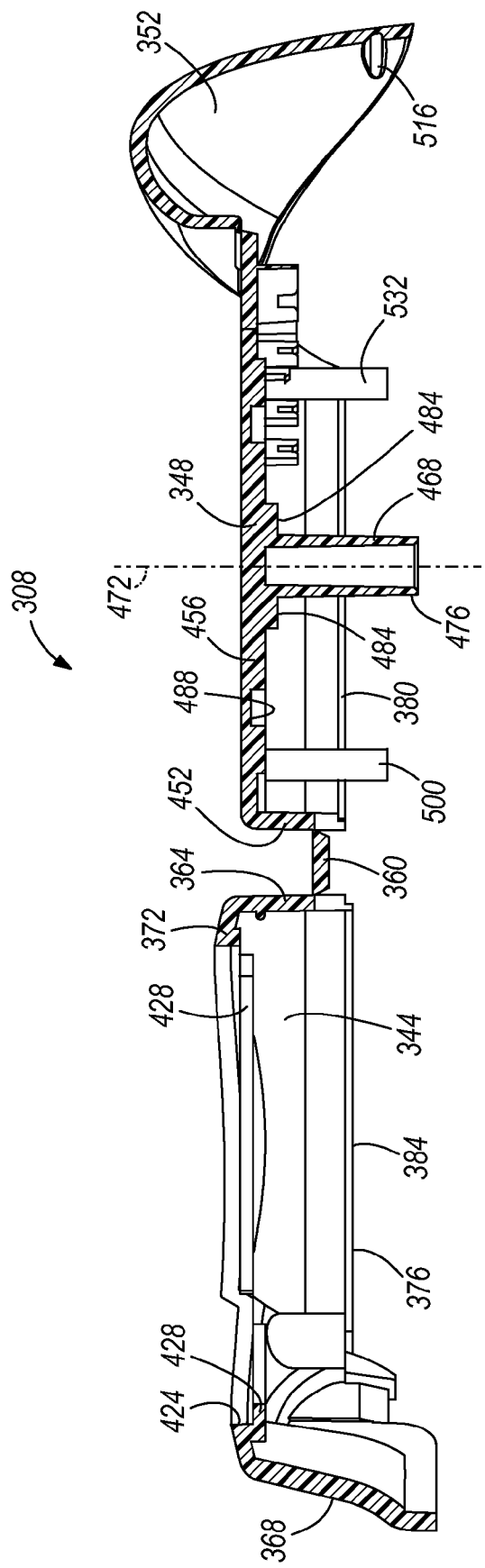
Figure 13:
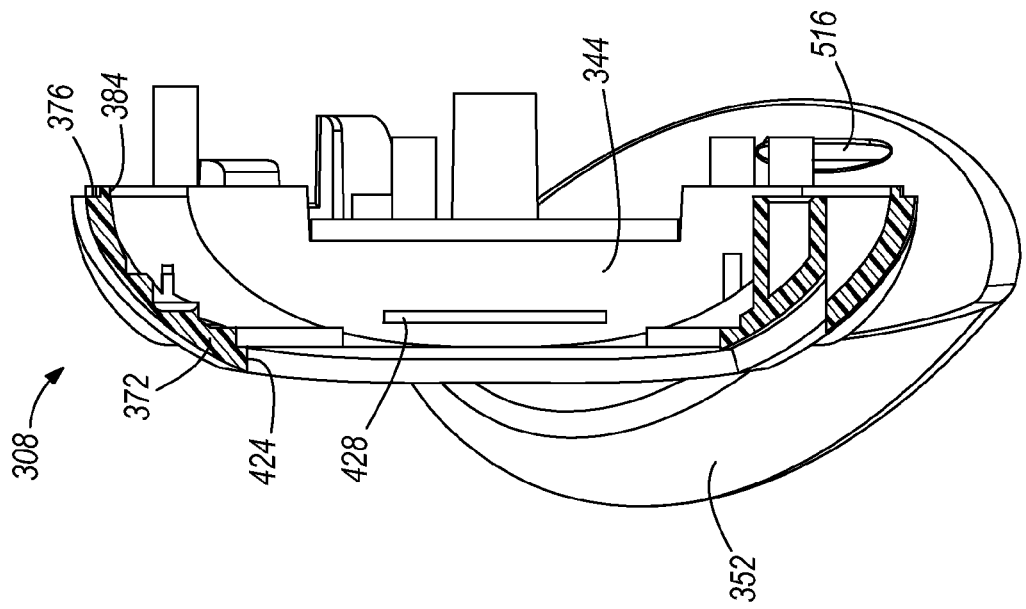

As shown in FIGS. 10a, 11, and 13, the front portion 344 also defines a window recess 424 that receives the window panel 356 (see FIGS. 14a-16). The window recess 424 is at least partially defined by the front wall 372 and permits the user to observe the amount of floss 10 remaining in the floss supply 304. In the illustrated construction, the window recess 424 includes a combination of lips, grooves, and locking tabs 428 that extend along at least a portion of the periphery of the recess 424 to secure the window panel 356 within the recess 424.

Figure 8E:
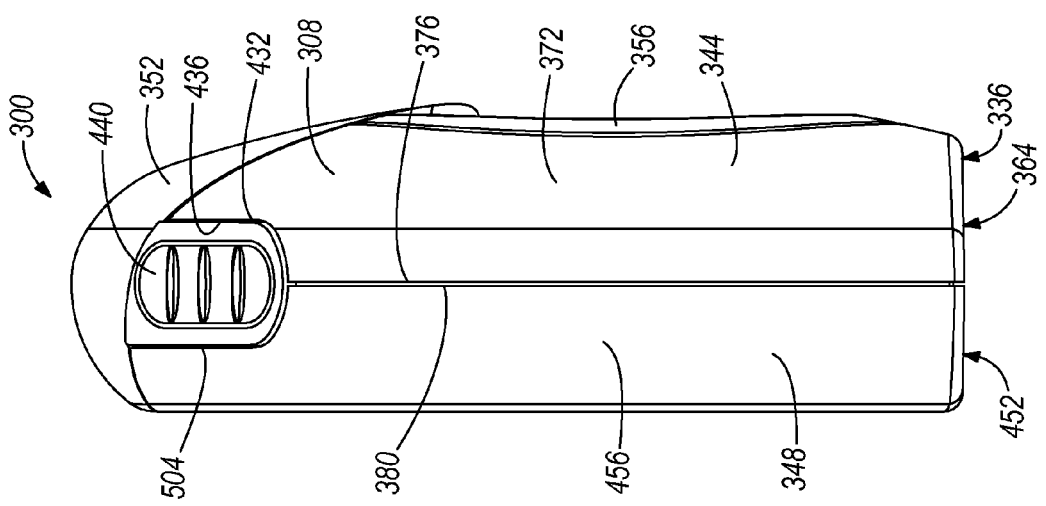

As shown in FIG. 8e, the front portion 344 defines a notch 432 that is recessed relative to the periphery 376 proximate the top wall 368. When the housing 308 is assembled, the notch 432 aligns with a corresponding notch 504 that is defined by the rear portion 348 to define a recess 436 that receives a reset button 440. The recess 436 is slightly larger than the reset button 440 to allow the button 440 to move or slide within the recess 436.

As shown in FIG. 10a, the front and rear portions 344, 348 each define a respective channel 444, 508 adjacent the notches 432, 504 that are configured to receive a portion of the reset button 440. When the housing 308 is assembled, the channels 444, 508 align with one another and cooperate to at least partially guide the movement of the reset button 440 relative to the housing 308 The reset button 440 is slideable along the channels 444, 508, although in alternate constructions the button 440 may pivot, rotate, or the like.

In the present invention, the channels 444, 508 are curvilinear in shape, generally defining a constant radius of curvature over their length; however, in alternate constructions, the channels 444, 508 may be linear or have varying radiuses of curvature. In still other constructions, the channels 444, 508 may include ridges or grooves to provide audible and/or tactile feedback as the reset button 440 moves relative to the housing 308. In still other constructions, ridges and/or grooves may be used to lock the reset button 440 into various predetermined positions.

Illustrated in FIGS. 10a-12, the rear portion 348 of the housing 308 includes a bottom wall 452 and a rear wall 456 extending upwardly from the bottom wall 452. As described above, the periphery 380 of the rear portion 348 substantially corresponds to the periphery 376 of the front portion 344 to produce the overall housing shape. Best illustrated in FIG. 10a, the rear portion 348 includes an alignment channel 460 extending along at least a portion of the periphery 380 to receive the alignment ridge 384 of the front portion 344. In the illustrated construction, at least a portion of rear wall 456 is substantially planar, to allow the housing 308 to lay flat on a support surface in a horizontal orientation.

The bottom wall 452 of the rear portion 348 is substantially semi-elliptical in shape, having a curvilinear edge that at least partially defines the contour of the rear wall 456. The bottom wall 452 is substantially planar, being configured to rest upon a support surface (e.g., a table top) and maintain the floss dispenser 300 in a substantially vertical orientation. In some constructions, the bottom wall 452 may include feet or be coated in a high friction material (e.g., rubber) to help stabilize the floss dispenser 300 on a support surface.

Figure 9:
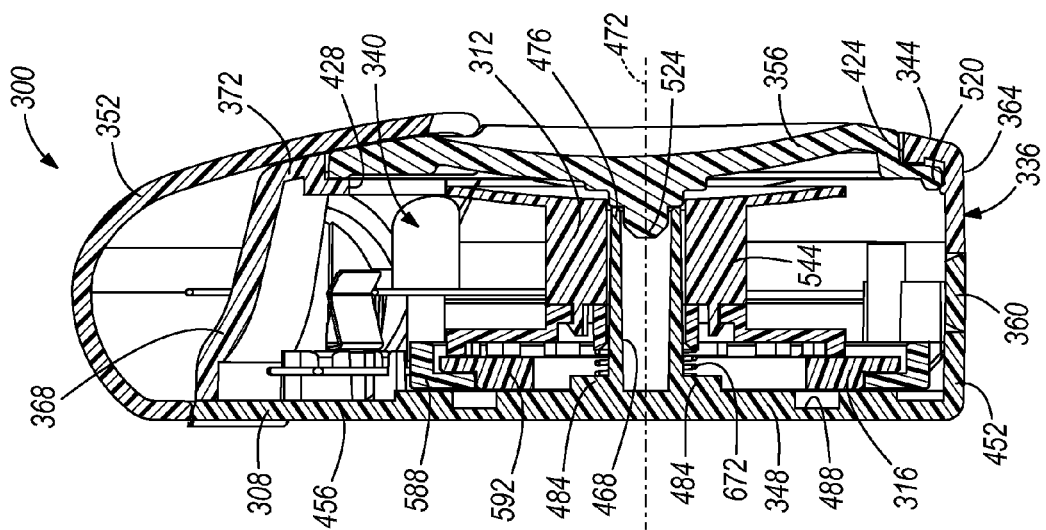
Figure 12:
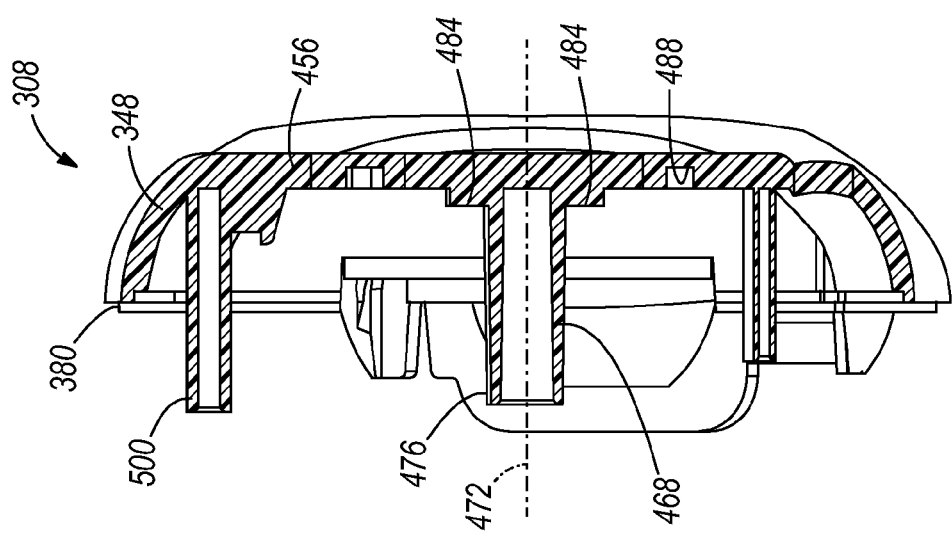

As shown in FIGS. 9, 11, and 12, the rear portion 348 includes a cylindrical shaft 468 extending substantially perpendicularly to the rear wall 456 and defining an axis 472. When the floss dispenser 300 is assembled, the shaft 468 supports the supply spool 312 for rotation about the axis 472. The shaft 468 may be coated with a low friction material or include bearings (not shown) to reduce rotational friction between the spool 312 and the shaft 468.

The rear portion 348 also includes a plurality of circumferentially spaced apart ribs 484 extending radially outwardly from the shaft 468 and axially away from the rear wall 456. The ribs 484 position the supply spool 312 a distance from the rear wall 456 to provide clearance for the locking mechanism 316 as discussed further below.

As best shown in FIGS. 9, 10a, and 11, the rear portion 348 of the housing 308 also defines a substantially annular and recessed track 488 defined by the rear wall 456 and substantially concentric with the axis 472. The track 488 includes a locking projection 492 extending radially inwardly from the outer diameter of the track 488 and substantially radially aligned with the notch 504 defining the recess 436 that receives the reset button 440 (see FIG. 8a). In the illustrated construction, the projection 492 is substantially triangular in shape, however alternate shapes may be used. The projection 492 is accompanied by a corresponding side-cut or bypass recess 496 extending radially inwardly from the inner diameter of the track 488 substantially opposite the projection 492. In the illustrated construction, the side-cut 496 is slightly radially off-set from the projection 492 in a counter-clockwise direction as viewed in FIG. 10a.

The rear portion 348 also includes a guide pin 500 extending substantially perpendicularly from the rear wall 456 and substantially radially opposed to locking projection 492 with respect to the axis 472. When the dispenser 300 is assembled, the guide pin 500 acts as a guide for movement of the carriage 588 within the housing 308.

Illustrated in FIGS. 9-11, and 32-33, the cap portion 352 of the housing 308 is substantially dome-like in shape. The cap portion 352 is pivotably coupled to the housing 308 (e.g., by a living hinge) and moveable between an open position, in which the top wall 368 is accessible by the user (see FIG. 32), and a closed position, in which the top wall 368 is covered (see FIG. 33). The cap portion 352 protects the floss 10 positioned outside the storage volume 340 during storage or non-use.

The cap portion 352 also includes a locking groove 516 formed in the inner surface of the cap 352. The locking groove 516 fits over a locking ridge 528 formed on the window panel 356 (see FIG. 14a) to lock or maintain the cap portion 352 in the closed position. In alternate constructions, the cap portion 352 may be maintained in the closed position by any one of a locking tab, reusable adhesive, snap, or the like.

Illustrated in FIGS. 14a-16, the window panel 356 of the housing 308 is generally oval-shaped and formed from a transparent material. The window panel 356 includes a lip 520 that extends about ¾ of the way around the panel's periphery to retain the window panel 356 within the window recess 424. The window panel 356 also includes an axially extending alignment boss 524 that extends into the storage volume 340 of the housing 308 and that is at least partially received within the distal end 476 of the shaft 468 when the floss dispenser 300 is assembled. The window panel 356 also includes a ledge 452 (see FIGS. 14b-14d) positioned proximate the periphery of the panel 356 and axially extending into the storage volume 340 to guide the floss 304 onto the roller 540 as the floss 304 is being removed from the spool 312. In the illustrated construction, the outer surface of the window panel 356 corresponds to the curvature of the surrounding front wall 372, giving the assembled housing 308 an aesthetically appealing appearance.

Figure 30:
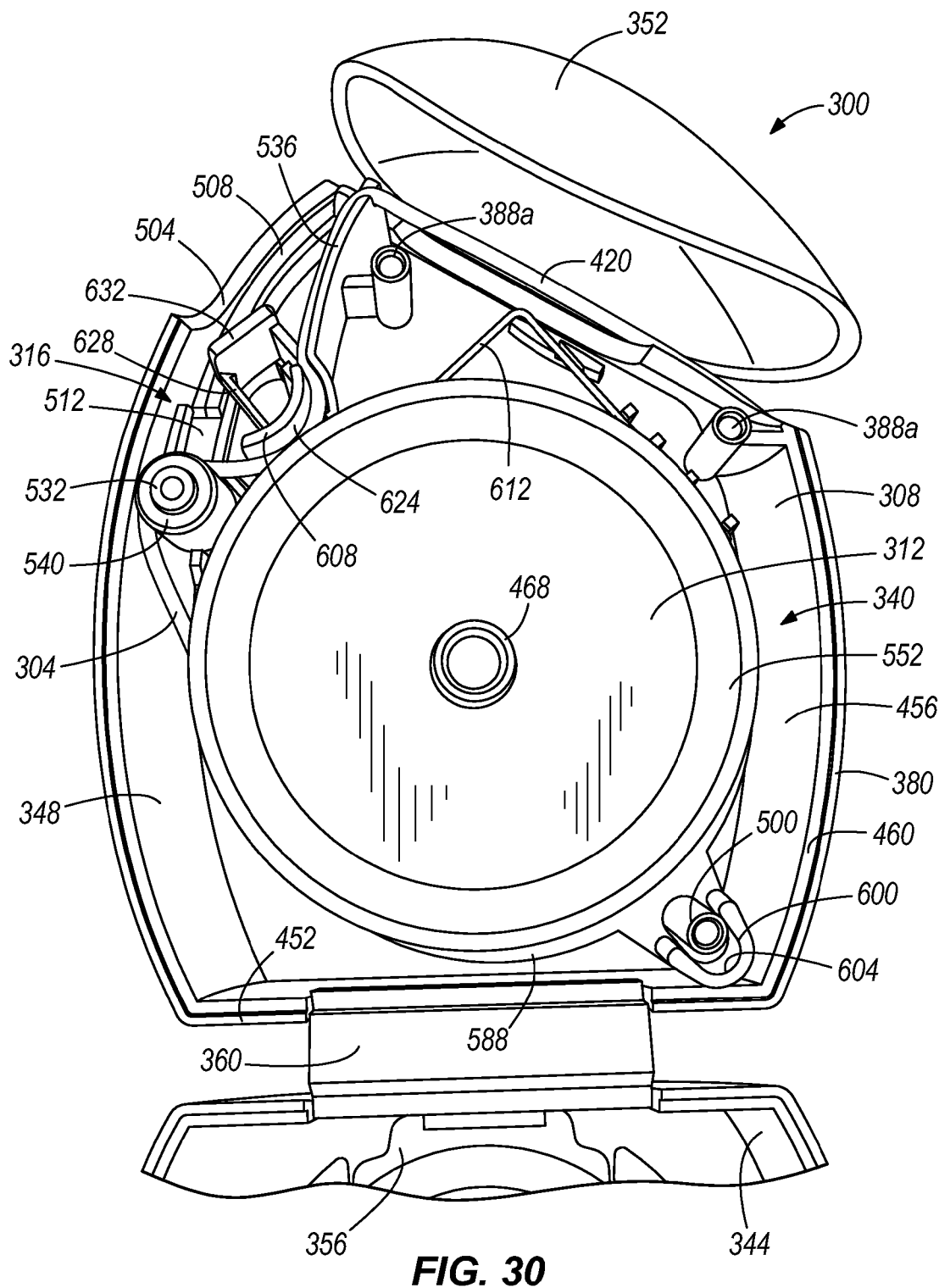
FIG. 30 is a front view of the dispenser of FIG. 8a with the front portion removed and the carriage in a first position.
Figure 31:
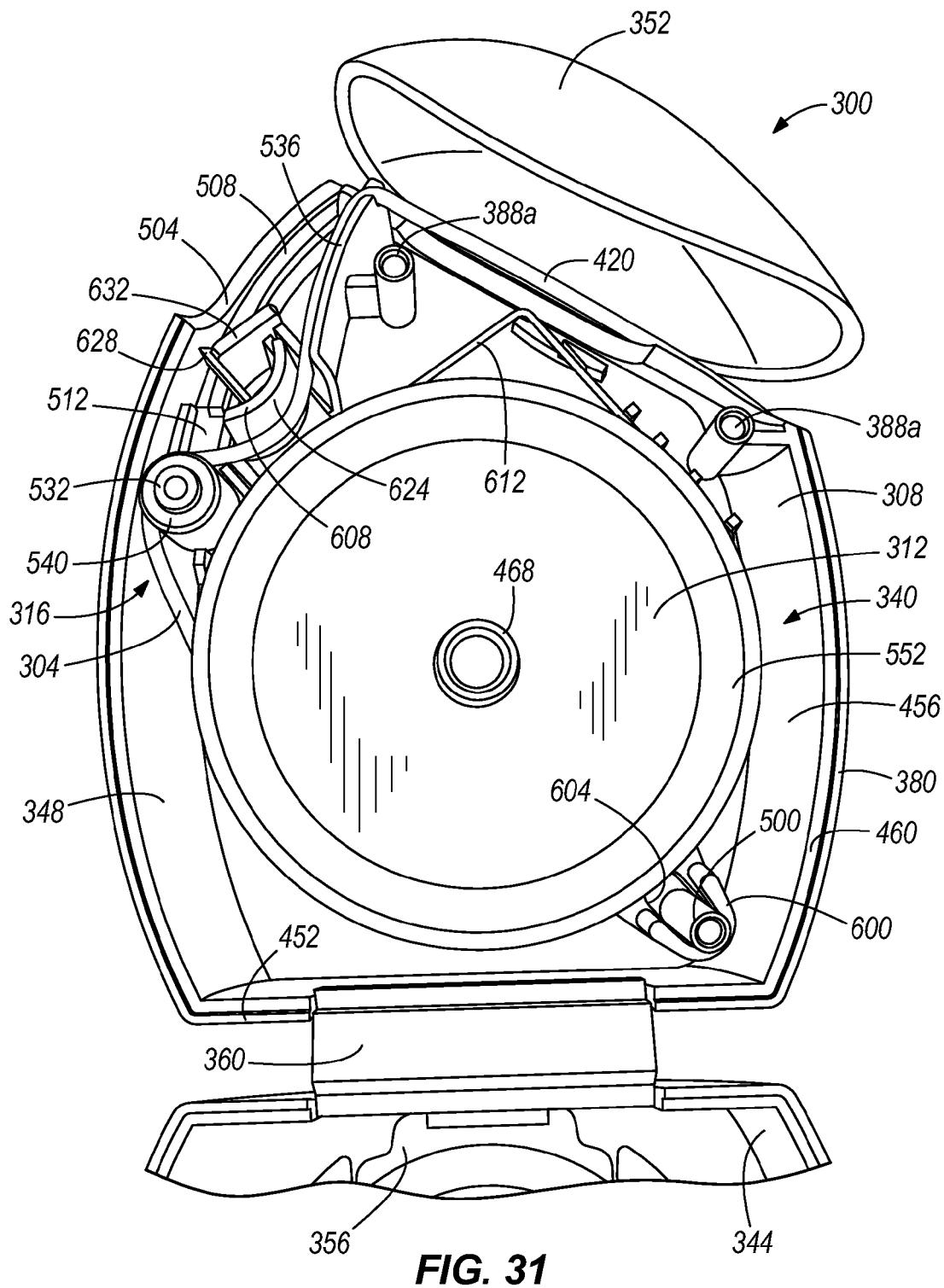
FIG. 31 is a front view of the dispenser of FIG. 8a with the front portion removed and the carriage in a second position.

With reference also to FIGS. 30 and 31, the housing 308 includes a first alignment member in the form of a spindle 532, and a second alignment member in the form of a guide wall 536. In the illustrated construction, the spindle 532 rotatably supports a roller 540 (see FIGS. 17a-18) at a location adjacent the periphery 380 within the storage volume 340. The guide wall 536 is curved and extends inwardly into the storage volume 340 from the opening 412 when the front and rear portions 344, 348 are brought together. The roller 540 and guide wall 536 are positioned to direct the floss 10 between the supply spool 312 and the opening 412. More specifically, the roller 540 and guide wall 536 are spaced from one another and work in tandem with the carriage 588 to adjust the locking mechanism 316 between the locked and unlocked configurations, as discussed further below.

Figure 18:
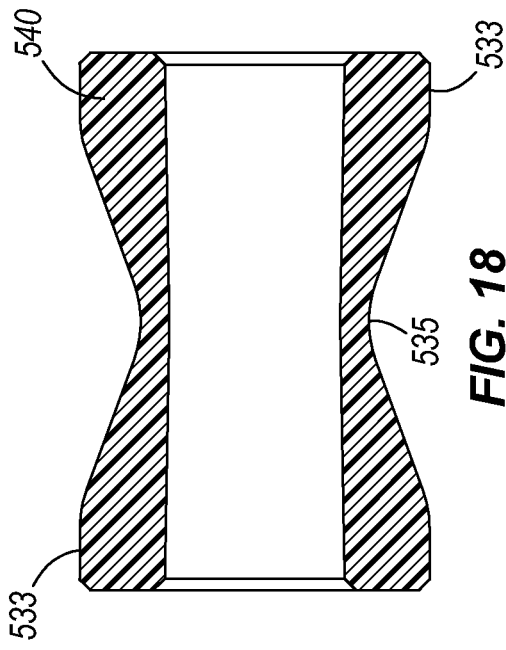
Figure 17A:
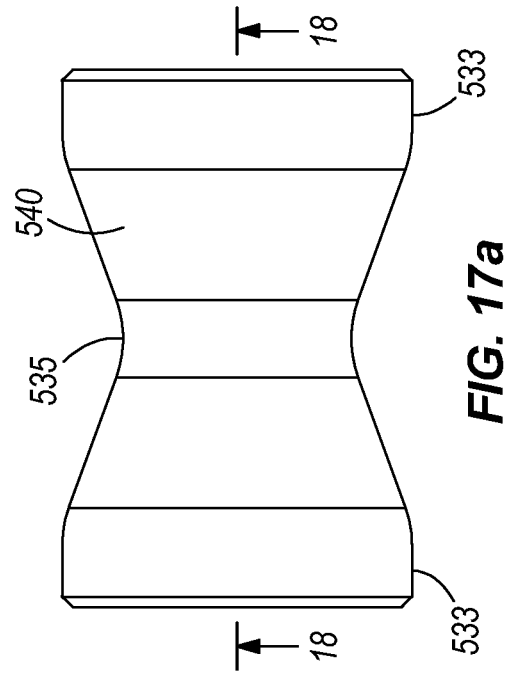
Figure 17B:
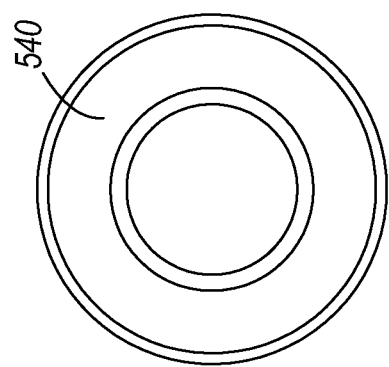

In the illustrated construction, the roller 540 is self-centering, having a profile that tapers from enlarged ends 533 to a reduced center portion 535 (see FIG. 18).

With reference to FIGS. 19a-21, the supply spool 312 includes a cylindrical core 544 defining a central recess or bore 548, a first flange 552 extending radially from a first end of the cylindrical core 544, and a second flange 556 extend radially from a second end of the cylindrical core 544. In some constructions, the diameter of the supply spool 312 may be greater than a typical dental floss spool. In this way, the curvature of the relatively stiffer portions of the floss 10 removed from the spool 312 is reduced. In the illustrated construction, the supply spool 312 is formed from a first and second portion 560, 564, each coupled to one another by a plurality of locking tabs 568. In other constructions, the supply spool 312 may be formed as a single piece. The central bore 548 of the supply spool 312 is sized to receive at least a portion of the shaft 468, thereby allowing the supply spool 312 to rotate about the axis 472 with respect to the housing 308.

Figure 19A:
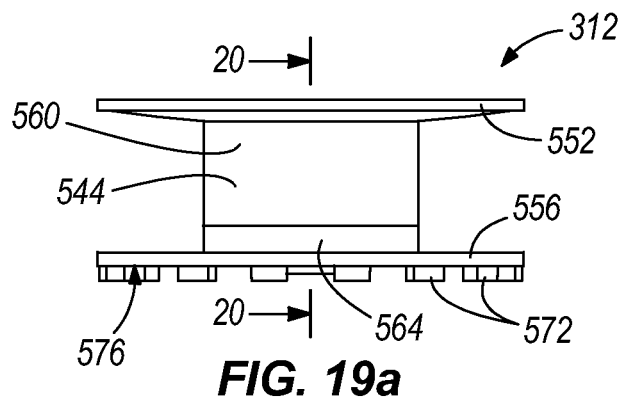
Figure 19B:
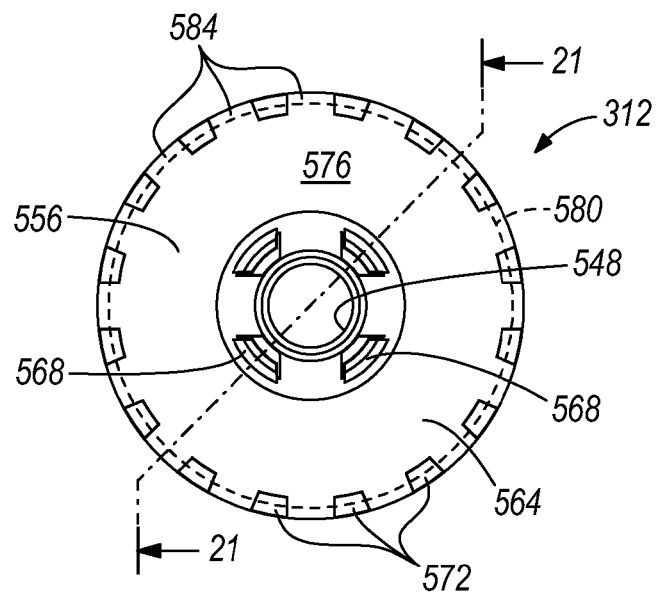
Figure 19C:
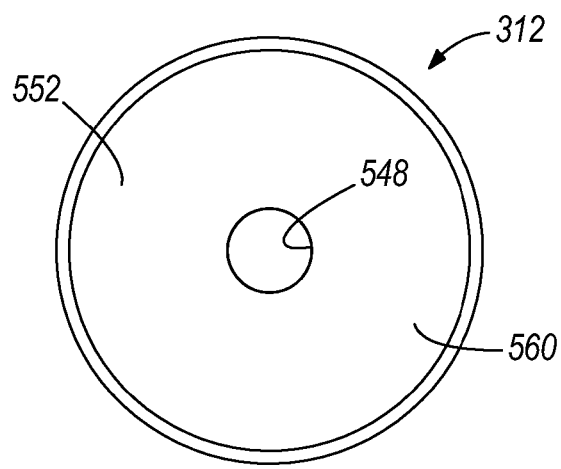
Figure 20:
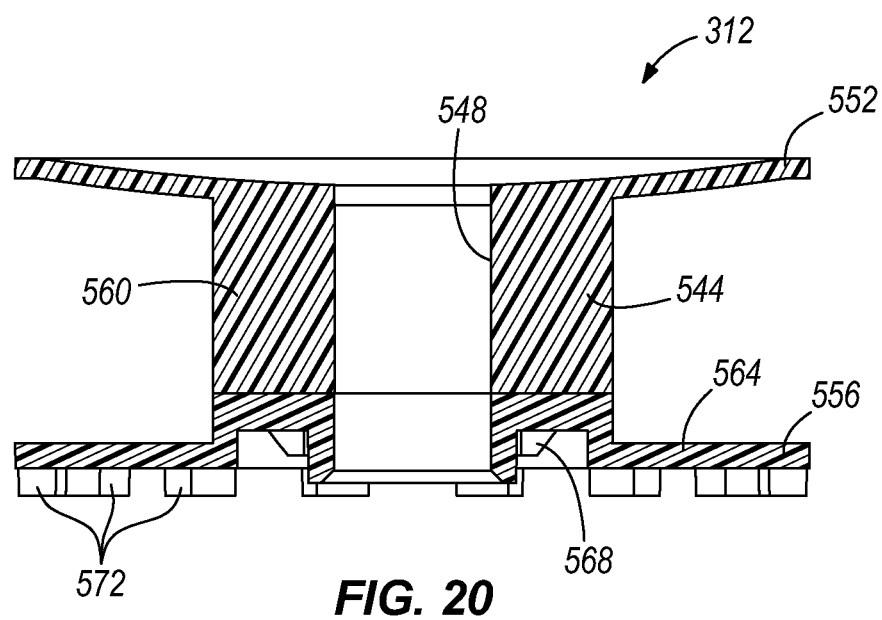
Figure 21:
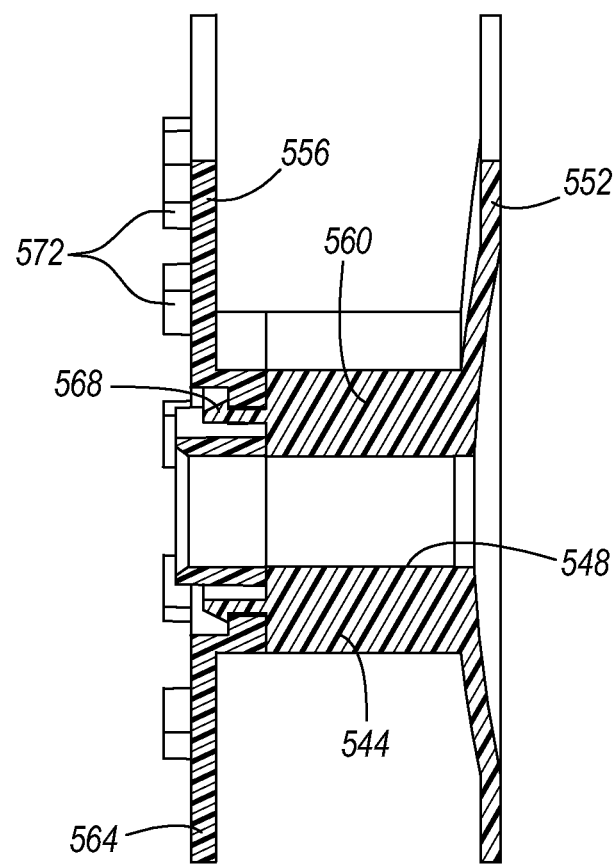
FIG. 21 is a section view taken along line 21-21 of FIG. 19b.

The supply spool 312 also includes a plurality of teeth 572, each extending axially from the bottom surface 576 of the second flange 556 (see FIGS. 19a and 19b). The teeth 572 are spaced evenly over the circumference of a first reference circle 580 that is concentric with the cylindrical core 544 and define a plurality of gaps 584 therebetween.

Figure 27:
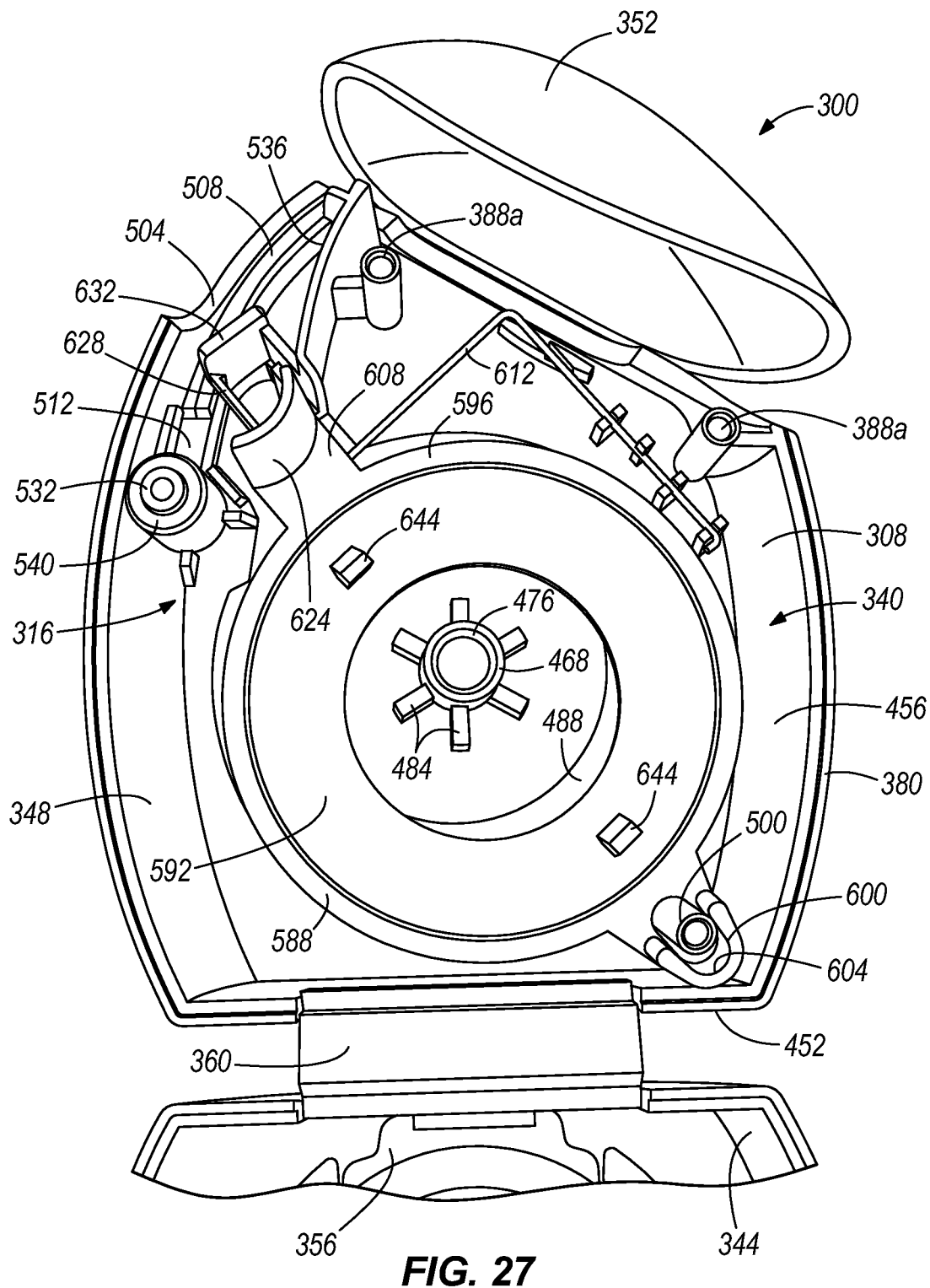
FIG. 27 is a front view of the dispenser of FIG. 8a with the front portion and the supply spool removed to show the carriage in a first position.
Figure 28:
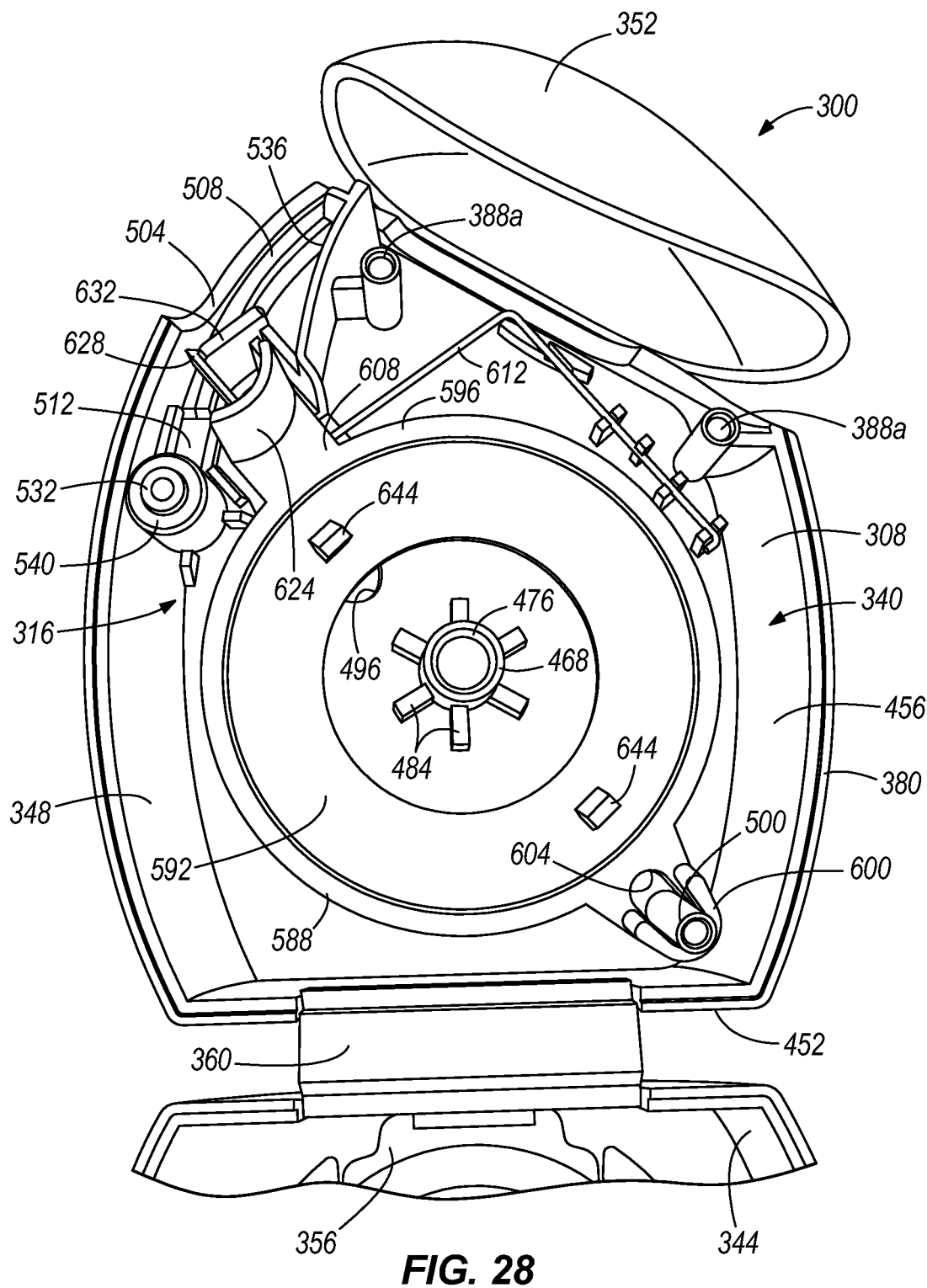
FIG. 28 is a front view of the dispenser of FIG. 8a with the front portion and the supply spool removed to show the carriage in a second position.
Figure 29E:
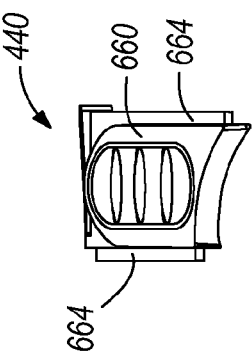
Figure 29B:
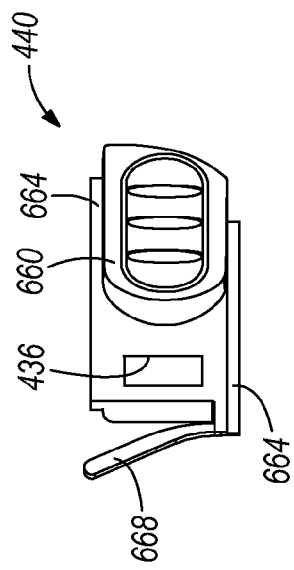
Figure 29A:
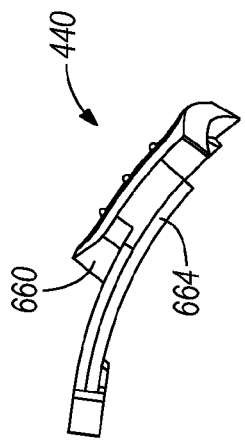
Figure 29C:
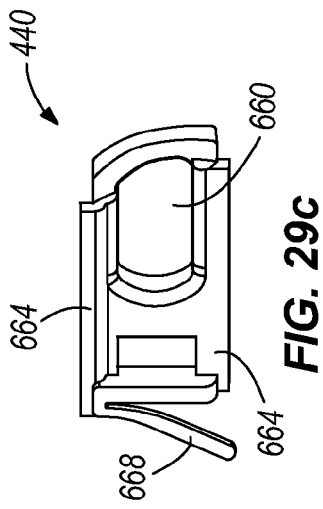
Figure 29D:
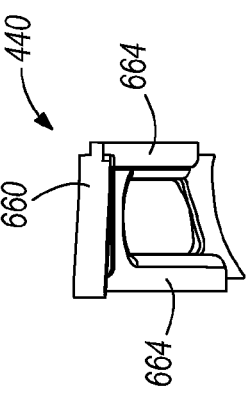

With reference to FIGS. 27 and 28, the locking mechanism 316 includes a carriage 588, a disk 592 rotatable with respect to the carriage 588, and a reset button 440. As described above, the locking mechanism 316 controls the amount of floss 10 that can be removed from the housing 308 at any one time by changing between an unlocked configuration, in which floss 10 can be freely removed from the housing 308, and a locked configuration, in which a limited amount or no floss 10 can be removed from the housing 308. The locking mechanism 316 controls the removal of floss 10 from the floss supply 304 by selectively allowing and preventing rotation of the supply spool 312 with respect to the housing 308. When the locking mechanism 316 is in the unlocked configuration, the supply spool 312 is free to rotate with respect to the housing 308. When the locking mechanism 316 is in the locked configuration, rotation of the supply spool 312 is limited or restricted. In alternative embodiments, the locking mechanism 316 may control the removal of floss 10 from the floss supply 304 by, for example, directly engaging the floss 10, automatically severing the floss 10 from the floss supply 304 when a desired floss fragment 320 has been removed, or the like.

Referring also to FIGS. 22a-24, the carriage 588 of the locking mechanism 316 includes a generally circular main body 596, a first arm 600 extending radially from one end of the main body 596, and a second arm 608 extending radially from an opposite end of the body 596 opposite the first arm 600. The main body 596 includes an annular wall 616 defining an inner and outer diameter, and a generally cylindrical outer wall 620 extending upwardly from the outer diameter of the annular wall 616. The annular wall 616 and the outer wall 620 are sized and configured to receive the disk 592 in a manner that allows the disk 592 to rotate freely with within the carriage 588 while maintaining substantially concentric alignment of the disk 592 with the main body 596.

The first arm 600 of the carriage 588 defines an elongated slot 604 that receives the guide pin 500 (see FIGS. 27 and 28). The second arm 608 defines a convex floss engaging surface 624 that cooperates with the first and second alignment members 532, 536 to define a serpentine path through which the floss 10 travels (see FIGS. 30 and 31) when pulled from the supply spool 312 and drawn through the opening 412. In the illustrated construction, the floss engaging surface 624 is curved, producing a smooth transition between the first and second alignment members 532, 536. However, in alternate constructions, the floss engaging surface 624 may include a pulley or define a groove. The second arm 608 also includes a radially-extending locking tab 628.

The carriage 588 is moveable in a generally linear direction between a first position in which the main body 596 is eccentric relative to the axis 472 (see FIG. 27), and a second position in which the main body 596 is concentric with the axis 472 (see FIG. 28). Movement of the carriage 588 is guided and limited at least partially by movement of the guide pin 500 within the slot 604 in the first arm 600. A biasing member 612 is secured within the housing 308 and, in the illustrated construction, engages the second arm 608 to bias the carriage 588 toward the first position.

As shown in FIGS. 25a-26, the disk 592 is substantially annular and includes a cylindrical core 636 defining a first outer diameter, and a flange 640 extending radially outwardly from a first end of the core 636 to define a second outer diameter greater than the first outer diameter. The disk 592 also includes a pair of protrusions 644 extending axially from the flange 640. The protrusions 644 are substantially diametrically opposed to one another and are spaced by a distance that corresponds to the diameter of the reference circle 580 associated with the teeth 572 of the supply spool 312. The disk 592 also includes a stopping lug 652 extending axially from the cylindrical core 636 of the disk 592. The lug 652 includes a ramped edge 656 along one side. As mentioned above, the disk 592 is received by the main body 596 and is moveable therewith between the first and second positions.

With reference to FIGS. 29a-29e, the reset button 440 includes a main body 660, a pair of ridges 664, a biasing member 668, and a release aperture 438. The ridges 664 extend outwardly from the body 660 and are slidingly received within the channels 444, 508 of the front and rear housing portions 344, 348, respectively. The biasing member 668 includes a spring-like arm extending from the body 660, the distal end of which is received by the anchor recess 512 of the housing 308. In alternate constructions, a spring, rubber band, or other form of biasing member may be utilized in place of the biasing member 668. The release aperture 438 is generally rectangular and is positioned between the main body 660, the ridges 664, and the biasing member 668.

When the dispenser is assembled, the reset button 440 is moveable between an upward, neutral position and a lowered, resetting position. For this purpose, a portion of the body 660 extends through the recess 436 so the user can manual actuate the reset button 440, e.g., move it generally downwardly to the resetting position, from outside the housing 308. The reset button 440 also is located and configured such that, when the cap portion 352 of the housing 308 is closed, the cap portion 352 engages the reset button 440 and similarly moves it generally downwardly to the resetting position. The outer portion of the body 660 may include grooves, or be coated in a high friction material (e.g., rubber) to aid the user in manually actuating the button 440.

As discussed further below, when the reset button 440 is moved from the neutral position to the resetting position, it changes the floss dispenser 300 from the locked configuration, in which the floss 10 may not be removed from the dispenser 300, to the unlocked configuration, in which floss 10 may be removed from the dispenser 300.

To assemble the floss dispenser 300, the window panel 356 is positioned within the window recess 424 of the front wall 372. The cutting member 416 is then coupled to the top wall 368. The carriage 588 is positioned within the housing 308 by aligning the elongated slot 604 with the guide pin 500 of the rear wall 456, and positioning the second arm 608 between the first and second alignment members 532, 536. At this time, the biasing member 612 also may be coupled between the carriage 588 and the housing 308. The carriage 588 is then lowered into the storage volume 340 until it engages the rear wall 456. The biasing member 612 will thereafter bias the carriage toward the first position in which the main body 596 is eccentric relative to the axis 472 (see FIG. 27)

The disk 592 is then positioned within the body 596 of the carriage 588. Because the main body 596 is in the first, eccentric position, the lug 652 is positioned within the bypass 496 that extends radially inwardly from the annular track 488 (see FIG. 10a). The reset button 440 may then be installed by positioning the ridge 664 within the channel 508 of the rear portion 348, while simultaneously positioning the distal end of the biasing member 668 in the anchor recess 512. It should be appreciated that the reset button 440 may be installed before the carriage 588 and/or the disk 592, if desired. In some constructions, a biasing member in the form of a coil spring 672 is positioned about the shaft 468 and engages the ribs 484.

The supply spool 312 is then mounted on the shaft 468 and is thus concentrically fixed thereto. The spring 672 is therefore positioned between the spool 312 and the ribs 484. Upon assembly, the spring 672 is compressed between the spool 312 and the ribs 484 causing the spring 672 to bias the spool 312 axially upwardly against the window panel 356. The resulting contact between the window panel 356 and the spool 312 provides a modest amount of friction that subtly restricts or limits unwanted rotation of the spool 312 even though the spool 312 is otherwise allowed to rotate. For example, friction between the spool 312 and the window panel 356 can prevent the rotational momentum of the spool 312 from continuing to rotate the spool 312 when a user stops pulling on the floss 10.

When the carriage 588 and disk 592 are in the first, eccentric position, the protrusions 644 on the flange 640 of the disk 592 are radially offset with respect to the gaps 584 between the teeth 572 of the supply spool 312. As such, the supply spool 312 is substantially free to rotate about the shaft 468 while the disk 592 remains substantially stationary with the lug 652 positioned within the bypass 496 of the annular track 488.

Because the supply spool 312 is substantially freely rotatable, the floss 10 may be unwound from the spool 312 and positioned within the serpentine path defined between the first and second alignment members 532, 536 and the floss engaging surface 624. More specifically, the floss is extended over the first alignment member 532 (including the roller 540, if present), under the floss engaging surface 624, and along the second alignment member 536. The floss is then positioned in the opening 412 defined by the top wall 368 (see FIGS. 30 and 31). Upon initial assembly, it is preferred that the serpentine path between the first and second alignment members 532, 536 is occupied by the less stiff textured segment 14b of the floss 10.

To close the housing 308, the front portion 344 is pivoted about the hinge member 360 and mated to the rear portion 348, including alignment of the alignment pins/recesses 388a, 388b with one another, and alignment of the remaining ridge 664 of the reset button 440 with the channel 444 of the front portion 344. Similarly, the alignment boss 524 of the window panel 356 is positioned within the distal end 476 of the shaft 468.

So assembled, the end portion 420 of the floss 10 can be secured within the cutting member 416 and the cap portion 352 may be closed. With the carriage 588 in the first, eccentric position (see FIG. 27), the spool 312 is free to rotate to dispense floss 304 through the opening 412.) To remove a floss fragment 320 from the floss dispenser 300, the user pivots the cap portion 352 into the open position, thereby exposing the top wall 368 of the housing 308 and the end portion 420 of the floss. The user grasps and pulls the end portion 420, thereby rotating the spool to unwind the floss 10 from the floss supply 304 while withdrawing the floss 10 from the housing 308. As the floss is unwound from the spool 312 and exits the housing 308, it travels through the serpentine path defined by the first alignment member 532, the floss engaging surface 624, and the second alignment member 536.

Initially, the less-stiff textured segment 14b of the multi-texture floss 10 passes through the serpentine path and is removed from the storage volume 340. As the textured segment 14b is drawn through the serpentine path, the biasing member 612 applies a sufficient biasing force to maintain the carriage 588 in the first, eccentric position (FIG. 27). Once the textured segment 14b has passed through the serpentine path, the adjacent stiffer smooth segment 14a of the multi-texture floss 10 enter the serpentine path. The increased stiffness of the smooth segment 14a being drawn through the serpentine applies increased force against the floss engaging surface 624. This increased force is sufficient to overcome the biasing force applied by the biasing member 612 and shifts the carriage 588 from the first position (eccentric relative to the axis 472, FIG. 27) to the second position (concentric relative to the axis 472, FIG. 28). In this regard, the change in the stiffness of the floss being drawn through the serpentine path operates to shift the carriage 588 from the first position to the second position.

When the carriage 588 moves to the second position, the end of the locking tab 628 passes over and latches onto the partition 632, thereby locking the carriage 588 in the second position. The end of the locking tab 628 also extends at least partially into the release aperture 438 of the reset button 440.

With the carriage 588 and the disk 592 shifted to and held in the second position, the protrusions 644 of the disk 592 are moved into concentric alignment with the teeth 572 of the supply spool 312. The protrusions 644 mesh with the teeth 572 such that the disk 592 and the supply spool 312 are coupled together for rotation as a unit. The movement of the disk 592 from the first position to the second position also causes the lug 652 to move from the side-cut 496 into the annular portion of the track 488. Engagement between the ramped edge 656 of the lug 652 and the locking projection 492 urges the disk 592 in the clockwise direction as viewed in, for example, FIG. 10a, which further facilitates engagement of the protrusions 644 and the teeth 572. Once the protrusions 644 are engaged with teeth 572 of the supply spool 312, additional floss removal causes the spool 312 and the disk 592 to rotate such that the lug 652 travels along the track 488 in a clockwise direction.

After approximately one full rotation about the track 488, the lug 652 contacts the locking projection 492, which restricts further rotation of the disk 592 and the supply spool 312 about the axis 472 thus preventing the user from removing additional floss 10 from the housing 308. The circumference of the spool 312 and the length of the smooth segments 14a are selected such that the length of floss dispensed by one rotation of the spool 312 is less than the length of the smooth segments 14a. In some embodiments, the length of the smooth segments 14a and the circumference of the spool 312 are selected such that when the lug 652 engages the locking projection 492 and prevents further rotation of the spool 312, the next textured segment 14b is positioned within the serpentine path but has not yet been withdrawn through the opening 412 in the housing 308. In this way, there remains a portion of the smooth segment 14a extending between the opening 412 and the cutting member 416.

The user then uses the cutting member 416 in the traditional manner to cut the floss within the smooth segment 14a of the multi-texture floss 10. Cutting the floss in this manner forms the tail 332 of the floss fragment 320 that has just been removed from the housing 308, and leaves the leader 324 of the subsequent floss fragment 320 secured to the housing by the cutting member 416.

To remove a subsequent floss fragment 320 from the floss dispenser 300, the user moves the reset button 440 into the resetting position. When the reset button 440 is moved to the resetting position, an edge of the release aperture 438 contacts the end of the locking tab 628, thereby disengaging the locking tab 628 from the partition 632 and allowing the carriage 588 to return to the first position under the influence of the biasing member 612. As the carriage 588 moves toward the second, eccentric position, it carries the disk 592 with it, which moves the lug 652 back into the bypass 496. The contour of the bypass 496 advances the disk 592 in a clockwise direction and moves the lug 652 past the locking projection 492.

Also during movement of the carriage 588 toward the second position, the protrusions 644 of the disk 592 are moved out of alignment with the teeth 572 of the supply spool 312. As a result, the supply spool 312 and the disk 592 are no longer coupled for rotation together, and the supply spool 312 is able to rotate freely, thereby allowing a user to withdraw additional floss to form an additional floss fragment 320.

In some constructions, including the illustrated construction, the reset button 440 is configured such that closing the cap portion 352 of the housing 308 moves the reset button 440 to the resetting position and resets the floss dispenser 300.

FIGS. 34-43 illustrate an alternate embodiment of a floss dispenser 300' for dispensing the multi-texture floss 10. The floss dispenser 300' contains much of the same structure and has many of the same properties as the floss dispenser 300 illustrated in FIGS. 8a-33. Common elements have been given the same reference numbers with an added prime symbol. The following description focuses primarily upon structure and features of the floss dispenser 300' that differ from those of the floss dispenser 300.

Figure 39:
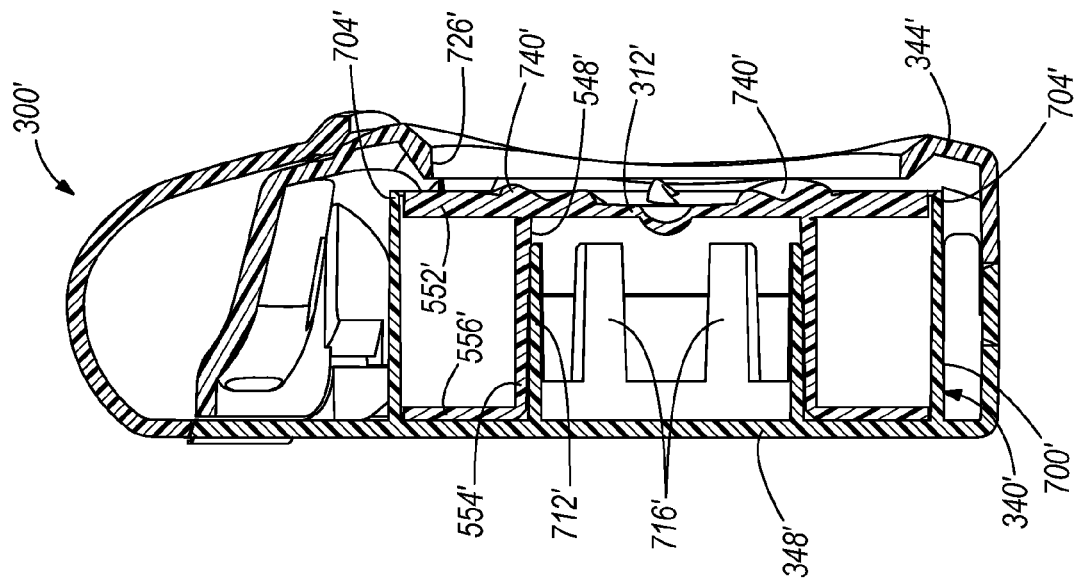
FIG. 39 is a section view taken along line 39-39 of FIG. 34.
Figure 38:
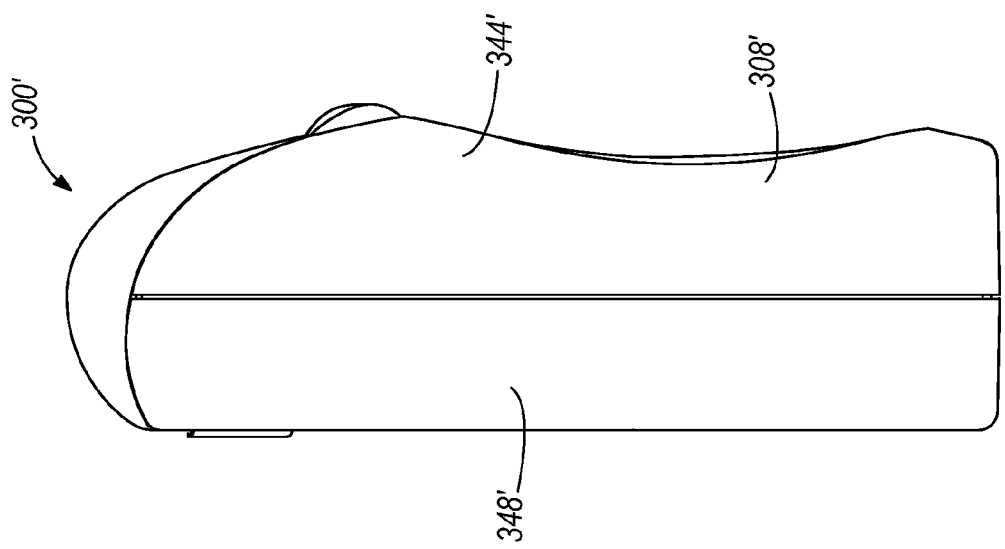
Figure 40:
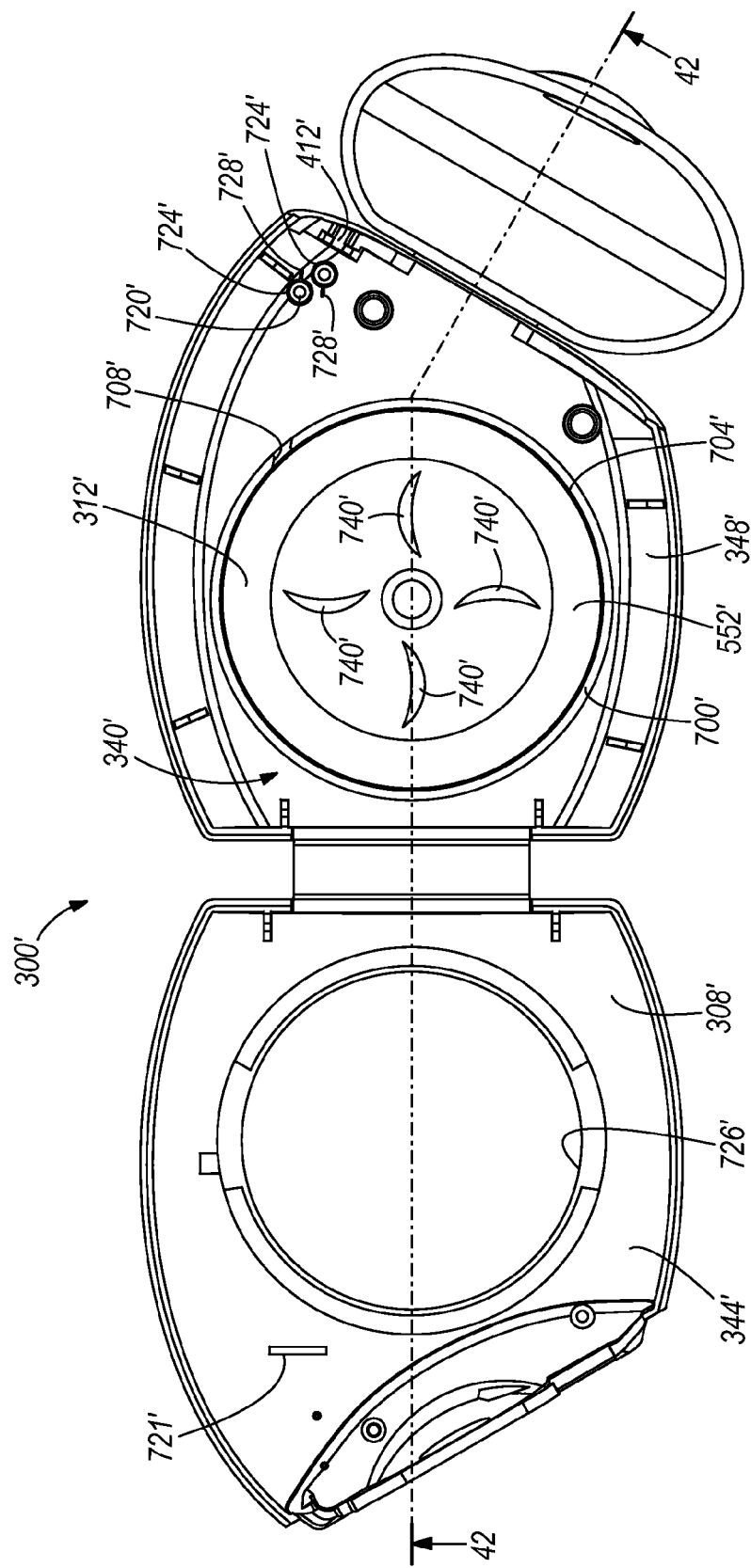
FIG. 40 shows the dispenser of FIG. 34 with the housing opened.
Figure 41:
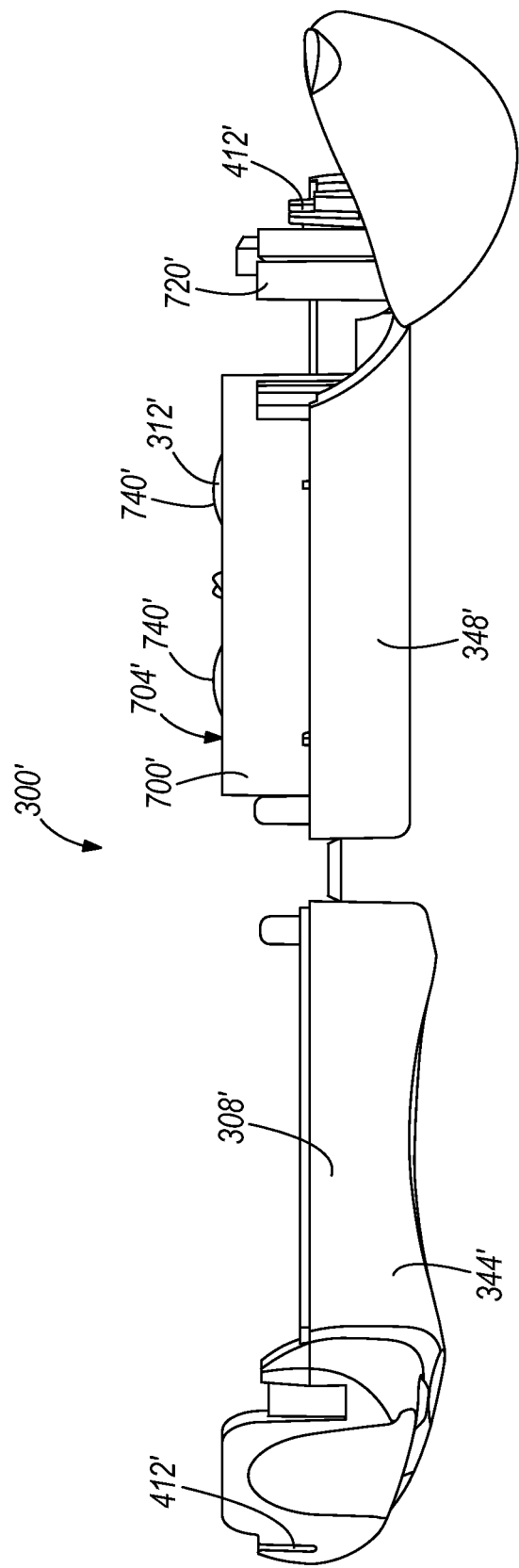
FIG. 41 is a side view of the dispenser of FIG. 40.
Figure 42:
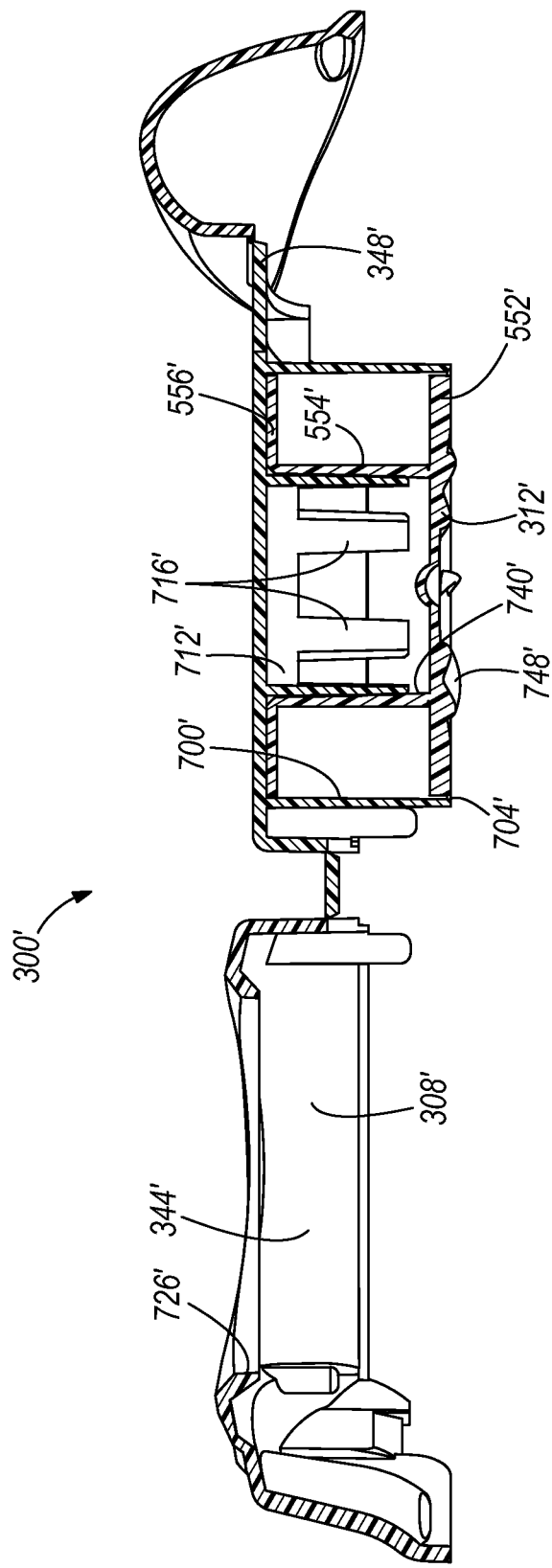
FIG. 42 is a section view taken along line 42-42 of FIG. 40.

Illustrated in FIGS. 39, 40, and 42, the rear portion 348' of the floss dispenser 300' includes an outer annular wall 700' extending substantially perpendicularly therefrom. The outer annular wall 700' is generally centered on and extends a distance from the rear portion 348' to define a distal edge 704' proximate the front portion 344' (see FIG. 39). The outer annular wall 700' also defines a slot 708' for floss 10 to pass therethrough.

The rear portion 348' also includes an inner annular wall 712' concentric with and positioned radially inward from the outer annular wall 700' (see FIG. 39). In the illustrated construction, the inner annular wall 712' includes a plurality of fingers 716', each extending substantially perpendicular from the rear portion 348'. When the dispenser 300' is assembled, the inner annular wall 712' and the outer annular wall 700' cooperate to define a substantially annular volume sized to at least partially receive a portion of the supply spool 312' therein.

The floss dispenser 300' also includes a metering element 720' positioned within the storage volume 340' and located between the slot 708' of the outer annular wall 700' and the opening 412'. During floss dispensing, the metering element 720' resists the removal of the floss 10 from the housing 308'. More specifically, the level of resistance provided by the metering element 720' varies dependent upon one or more properties of the section of floss 10 engaging the metering element 720'. The front portion 348' includes a wall 721' that, when the housing 308' is closed, is positioned between the slot 708' and the metering element '720 and guides the floss 10 toward the metering element '720. When the floss dispenser 300' is assembled, the floss 10 is routed away from the spool 312' by passing it through the slot 708' of the outer annular wall 700', through the metering element 720', and out the opening 412' so it can be grasped by the user (see FIG. 43).

In the illustrated construction, the level of resistance provided by the metering element 720' is dependent upon the stiffness of the section of floss 10 that is in engagement with the metering element 720'. More specifically, when the section of floss 10 in engagement with the metering element 720' has a first stiffness, a first resistance is produce that requires a first pulling force to remove the floss 10 from the dispenser 300'. Similarly, when the section of floss 10 in engagement with the metering element 720' has a second stiffness greater than the first stiffness, a second resistance is produced, greater than the first resistance, that requires a second pulling force, greater than the first pulling force, to remove the floss 10 from the dispenser 300'. In alternate constructions, the resistance provided by the metering element 720' may depend on other floss properties such as diameter, texture, material composition, and the like. In still other constructions, the resistance provided by the metering element '720 may be based on a combination of floss properties.

Figure 43:
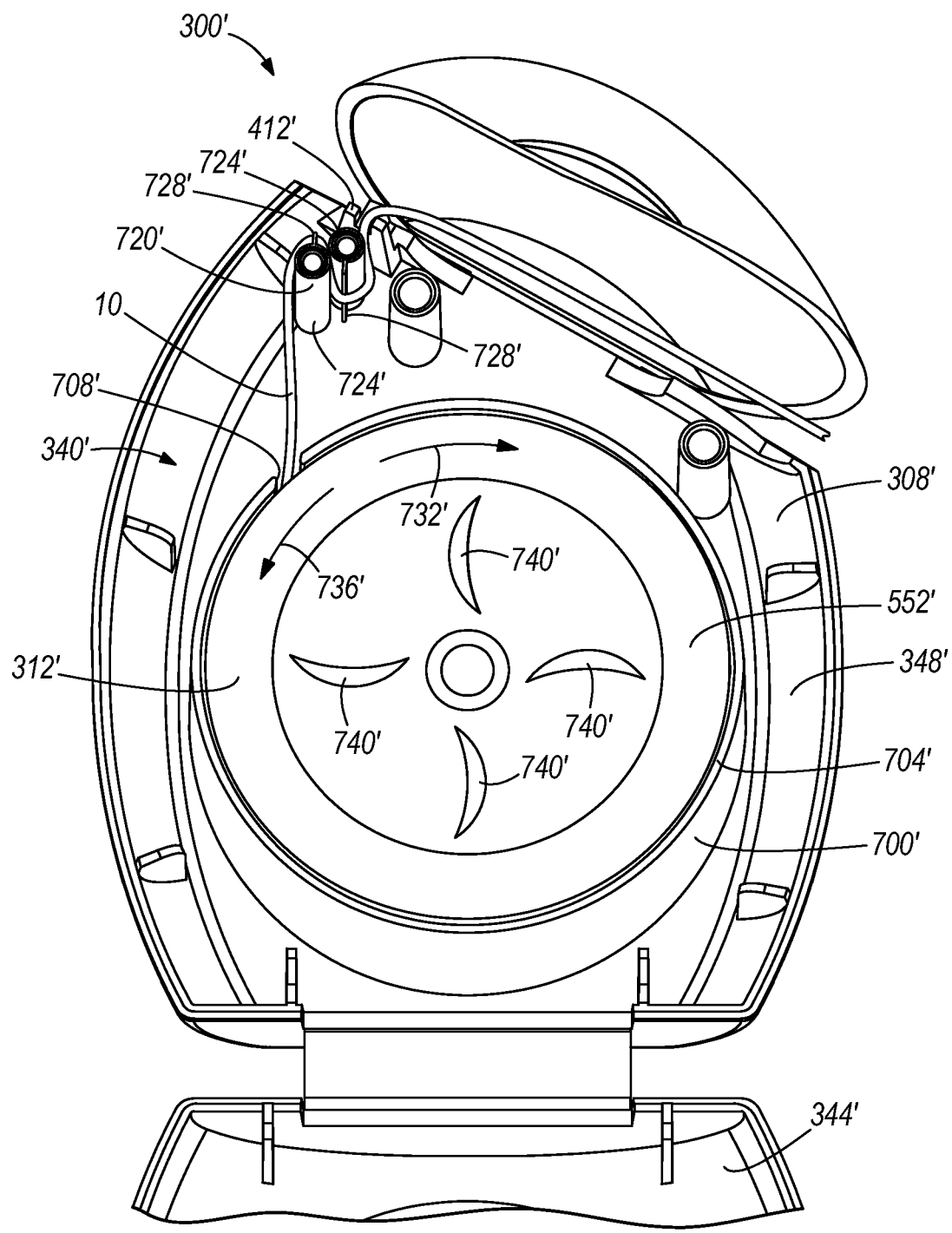
FIG. 43 shows the dispenser of FIG. 34 with the front portion removed.
Figure 44:
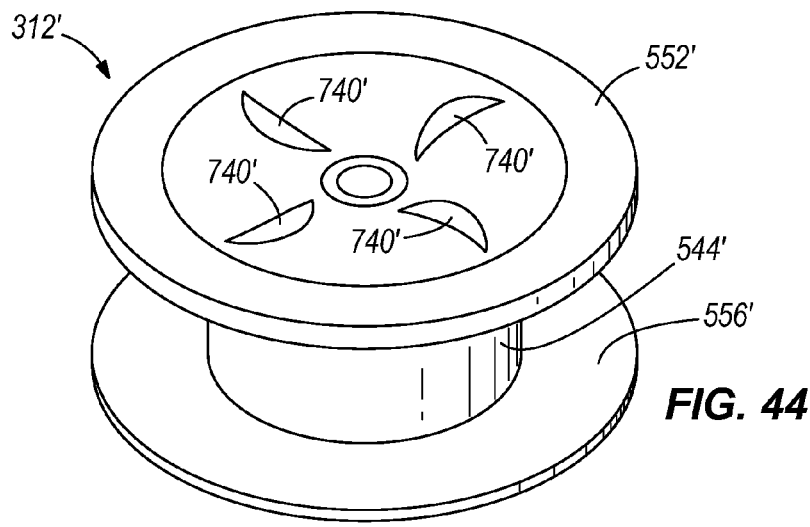
FIGS. 44-48 illustrate an alternate construction of the supply spool.
Figure 45:
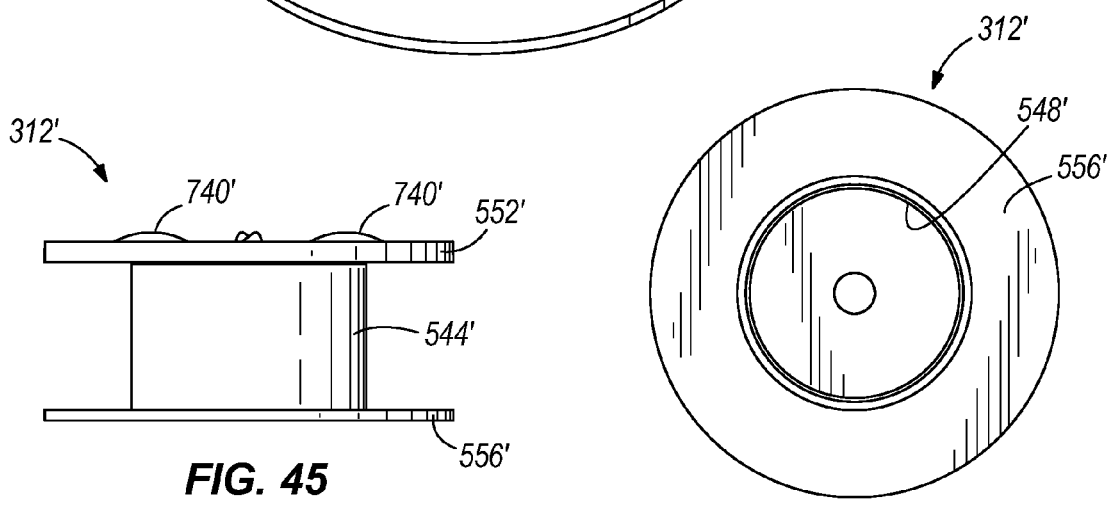
Figure 48:
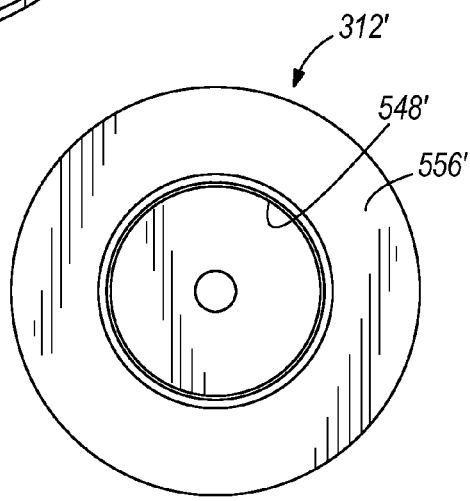
Figure 46:
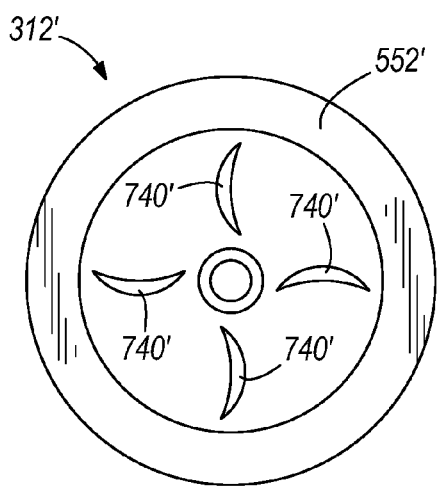
Figure 47:
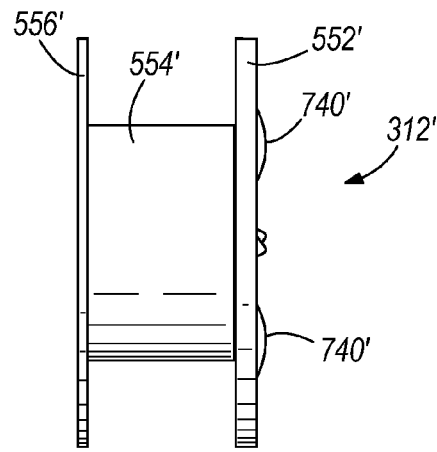

Illustrated in FIGS. 40 and 43, the metering element 720' includes a plurality (e.g., two) of substantially cylindrical protrusions 724' spaced a distance from one another and positioned between the slot 708' and the opening 412'. The illustrated protrusions 724' each include an optional thin wall 728' extending radially outwardly therefrom. When assembled, the floss 10 extends between the cylindrical protrusions 724' in a substantially serpentine path before exiting through the opening 412' (see FIG. 43). The orientation of the walls 728' and the distance between the cylindrical protrusions 724' cooperate to resist the movement of the floss 10 along the serpentine path. The distance between the cylindrical protrusions 724' and the orientation or stiffness of the walls 728' can be adjusted to alter the amount of resistance provided.

With reference also to FIGS. 44-48, the supply spool 312' includes a cylindrical core 544' defining a central recess or bore 548', a first flange 552' extending radially from a first end of the cylindrical core 544', and a second flange 556' extend radially from a second end of the cylindrical core 544'. In some constructions, the diameter of the supply spool 312' may be greater than a typical dental floss spool. In this way, the curvature of the relatively stiffer portions of the floss 10 removed from the spool 312' is reduced. The central bore 548' of the supply spool 312' is sized to receive at least a portion of the inner annular wall 712' therein, allowing the supply spool 312' to freely rotate in both directions about an axis with respect to the housing 308'. The outer diameters of the first flange 552' and the second flange 556' substantially correspond with the inner diameter of the outer annular wall 700' to stop floss from uncoiling from the spool 312' when then dispenser 300' is not in use.

The front portion 344' of the housing 308' defines an opening or aperture 726' that allows a user to manually engage and rotate the spool 312' to rewind floss, for example, when the user has pulled off more floss than he/she would like to use. Unlike standard floss dispensers, which would require the user to disassemble the housing in order to rewind inadvertently removed floss, the housing 308' is configured to permit the user to rewind the floss without having to disassemble or otherwise manipulate the housing 308'. When floss 10 is uncoiled from the spool 312', the spool 312' rotates in a first direction 732' with respect to the housing 308' (e.g., in the clockwise direction as viewed in FIG. 43). To rewind the floss onto the spool 312', the user can manually rotate the spool 312' in a second direction 736', opposite the first direction 732' (e.g., the counter-clockwise direction as viewed in FIG. 43), to coil the floss 10 back onto the spool 312' (see also FIG. 34). In the illustrated construction, the spool 312' includes a plurality (e.g., four) of ridges 740' that are radially spaced along the first flange 552' and that are accessible to the user through aperture 726' formed in the front portion 344' of the housing 308'. In the illustrated construction, the user can rotate the spool 312' in either direction by engaging the ridges 740' and manually rotating the spool 312'. Dependent upon the direction of rotation, this can cause the floss 10 to wind (e.g., by rotating in the second direction 736') or unwind (e.g., by rotating in the first direction 732') from the spool 312'.

While the illustrated embodiment includes an aperture 726' on a front face of the housing 308' that affords access to the first flange 552' of the spool 312', other embodiments may include an aperture on the side of the housing 308' that affords access to the outer diameter of the spool 312', or to some other portion of the spool. Also, different embodiments can include handles, cranks, projections, and other features that may be formed integral with or separate from the spool 312' and that permit a user to manually rotate the spool 312' at least in a direction that coils or winds the floss back onto the spool 312'.

To assemble the dispenser 300', a spool 312' with a length of floss 10 wound thereon is loaded into the housing 308', making sure the inner annular wall 712' is received within the bore 548' of the spool 312'. The floss 10 is then fed through the slot 708', passed through the serpentine path of the metering element 720' and fed through the opening 412'. The housing 308' can then be closed.

To operate the device, the user grasps the end of the floss 10 and pulls to begin dispensing the floss 10 from the housing 308'. When the less-stiff segment 14b of the multi-texture floss 10 is in engagement with the metering element 720' (e.g., the segment 14b is positioned in the serpentine path) and is being removed from the storage volume 340', pulling the floss 10 from the housing 308' requires the user to exert a pulling force having a first, relatively lower magnitude to withdraw the floss 10 from the housing 308'. Once the textured segment 14b has passed through the serpentine path, the adjacent stiffer segment 14a of the multi-texture floss 10 engages the metering element 720' and enters into the serpentine path. As the stiffer segment 14a passes through the serpentine path the resistance provided by the metering element 720' increases, thus, pulling the floss 10 from the housing 308' while the segment 14a is engaged with the metering element 720' requires the user to exert a pulling force having a second, relatively higher magnitude to withdraw the floss 10 from the housing 308'. Stated differently, as floss is being withdrawn from the housing 308', the user experiences an increase in resistance just before the stiffer segment 14a begins to emerge from the housing 308'. The differences in the resistance provided by the metering element 720' generally correspond to the differences in bending stiffness of the segments 14a and 14b, which is to say that the stiff segments 14a have a higher bending stiffness, and therefore a higher resistance to movement through serpentine path, than the segments 14b.

By providing the user with an indication that a stiffer segment 14a is about to emerge from the housing 308', the dispenser 300' aids the user in severing the floss in approximately the middle of the stiff segment 14a. By severing the floss in the middle of the stiff segment 14a, the user ends up with a length of floss where at least one end of the floss is relatively stiff and can be used as a "leader" or "threader" for inserting the end of the floss into interdental spaces, or into the spaces between braces, bridges, and other dental work that cannot be accessed using traditional flossing techniques. As discussed above, coloring can be applied to at least one of the segments 14a, 14b to further aid a user in severing the floss in the approximate middle of the stiff segment 14a. For example, by coloring the stiff segments 14a green and leaving the segments 14b white, or by coloring the segments a color other than green, a user can easily identify the stiff segments 14a and sever the floss appropriately.

If a user is diligent about repeatedly severing the floss in the approximate middle of the stiff segment 14a, he or she will consistently be provided with a length of floss where each end is relatively stiff and can be used as a "leader" or "threader." Of course, if the user wants to dispense multiple floss fragments without regard to where the floss is severed, the user can continue to remove floss from the dispenser 300' until the desired length is achieved. When this occurs, after the initial increase in resistance (e.g., corresponding to the stiff segment 14a engaging the metering element 720'), the resistance will reduce as a second less-stiff segment 14b, adjacent the first stiff segment 14a, enters the serpentine path and engages the metering element 720'. As such, the user will experience one resistance "bump" for each stiff segment 14a that is dispensed.

Figure 49:
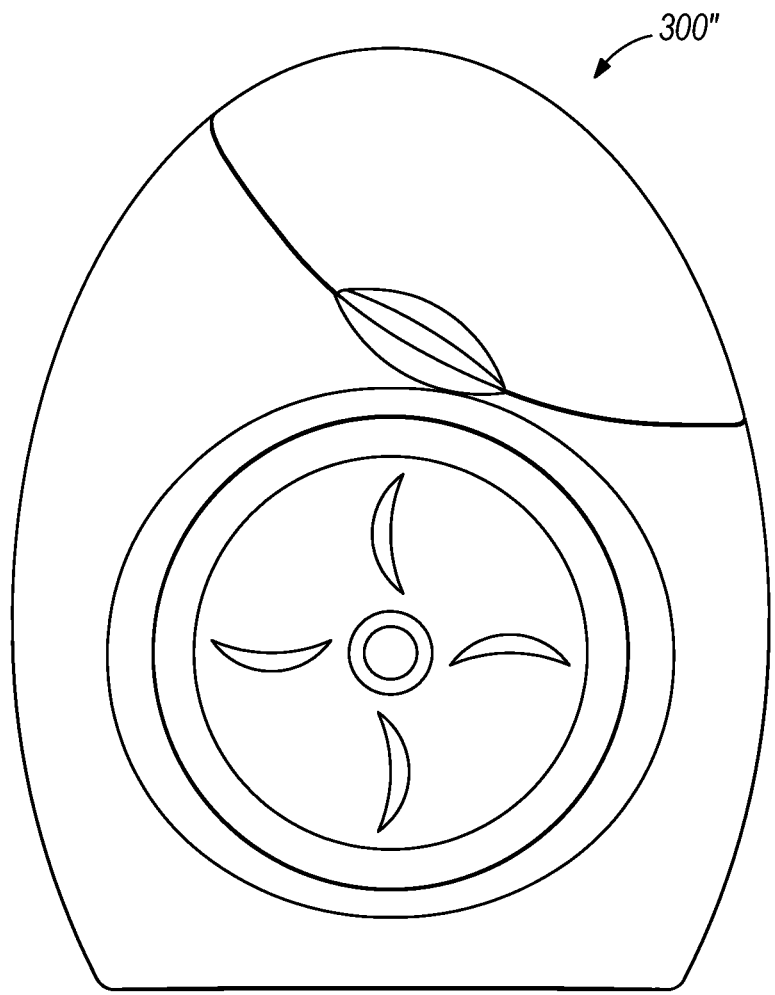
FIG. 49 is a front view an alternate construction of a dispenser for the multi-texture dental floss of FIG. 1.
Figure 51:
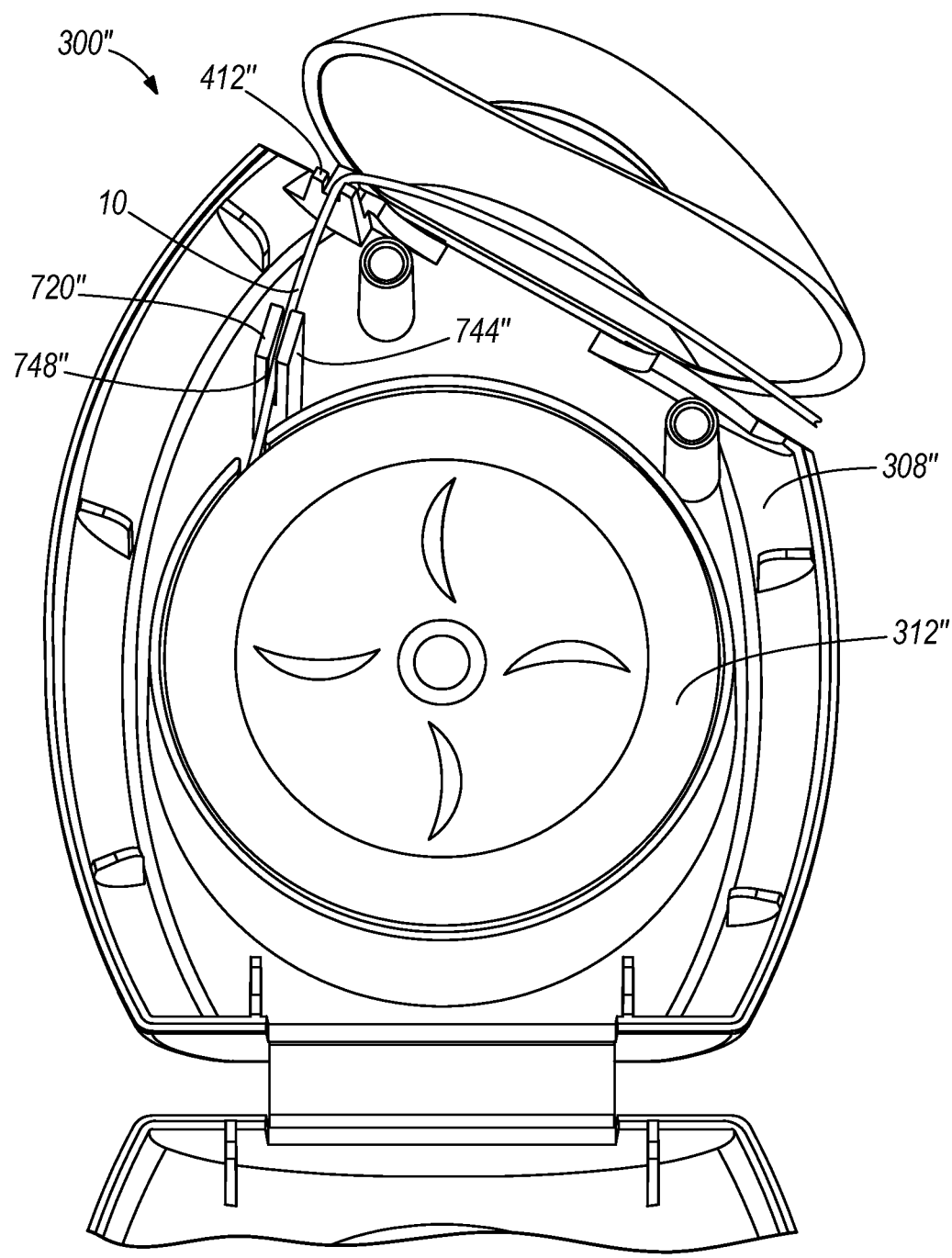
FIG. 51 illustrates the dispenser of FIG. 49 with the front portion removed.

FIGS. 49-51 illustrate an alternate embodiment of a floss dispenser 300" for dispensing the multi-texture floss 10. The floss dispenser 300" contains much of the same structure and has many of the same features as the floss dispenser 300' illustrated in FIGS. 34-43. Common elements have been given the same reference numbers with a double prime symbol. The following description focuses primarily upon structure and features of the dispenser 300" that are different from the dispenser 300'.

As shown in FIGS. 50 and 51, the metering element 720" of the dispenser 300" includes a protrusion 744" extending generally forwardly from the rear portion 348" and forming a groove 748" therein. Other embodiments may include a pair of resilient fingers extending forwardly from the rear portion 348" and defining the groove 748" therebetween. In either embodiment, the groove 748" is oriented substantially along an imaginary line extending between the slot 708" and the opening 412".

The front portion 344" of the housing includes a substantially rectangular and hollow box structure 750" that extends generally rearwardly from the front portion 344" and that is positioned and oriented to fit over the protrusion 744" when the front portion 344" is closed with respect to the rear portion 348". The box structure 750" functions as a clamping structure for controlling the width of the groove 748". When the dispenser 300" is assembled, the floss 10 passes through the slot 708", through the groove 748", and out the opening 412" where it can be grasped by the user.

The width of the groove 748" and its relationship with the dimensions of the floss 10 determine how much pulling force is required to withdraw the floss 10 from the housing 308". For example, making the groove 748" thinner will increase the resistance on the floss 10, and making the groove 748" thicker will reduce the resistance on the floss 10, assuming properties of the floss 10 stay constant. The width of the groove 748" and the pressure it applies to the floss 10 can be varied by changing the configuration of the protrusion 744" or by changing the configuration of the box structure 750". When the housing 308" is closed the box structure 750" receives the ends of the protrusion 744" and pinches them together. Thus, by narrowing the box structure 750", the groove 748" will also be narrowed once the housing 308" is closed. In some embodiments, a small insert (not shown) can be inserted into the box structure 750" to narrow the width of the box structure 750" and pinch the ends of the protrusion 744" closer together. In this way, the same housing, either with or without an insert, can be used to dispense spools carrying flosses of different thicknesses.

Like the dispenser 300', when the less stiff floss segment 14b is positioned in the groove 748", pulling the floss from the dispenser 300" requires the user to exert a pulling force having a first, relatively lower magnitude, and when the stiff floss segment 14a is positioned in the groove 748", the resistance on the floss increases and the user must apply a pulling force having a second, relatively higher magnitude. In the dispenser 300', the differences in the resistance provided by the metering element 720" generally correspond to the differences in resistance to compression of the segments 14a and 14b. Generally speaking, the treated stiff segments 14a are less deformable than the segments 14b, and when being drawn through the groove 748", the stiff segments 14a maintain a larger cross section than the segments 14b, which include fibers that are able to deform and flatten as they pass through the groove 748".

The invention claimed is:

1. A dental floss dispensing unit comprising:
   a housing;
   a supply spool coupled to the housing and having a length of floss wound thereabout, the length of floss including a free end extending from the housing; and
   a metering element coupled to the housing and operatively engaging a portion of the length of floss, wherein
   the metering element provides resistance against removal of the length of floss from the housing,
   a magnitude of the resistance against removal of the length of floss from the housing is dependent upon at least one property of the portion of the length of floss engaging the metering element, the supply spool rotates with respect to the housing during removal of the length of floss from the housing, and the magnitude of the resistance against removal of the length of floss from the housing is independent from rotation of the supply spool.

2. The dental floss dispensing unit of claim 1, wherein the at least one property of the portion of the length of floss engaging the metering element includes stiffness.

3. The dental floss dispensing unit of claim 1, wherein the metering element defines a serpentine path through which the length of floss extends.

4. The dental floss dispensing unit of claim 1, wherein the metering element defines groove, and wherein the length of floss extends through the groove.

5. The dental floss dispensing unit of claim 1, wherein the length of floss includes alternating first segments and second segments, the first segments having a first property and the second segments having a second property different from the first property.

6. The dental floss dispensing unit of claim 5, wherein the first property and the second property are associated with one of a stiffness, a thickness, and a texture of the respective first and second segments.

7. The dental floss dispensing unit of claim 6, wherein the first segments have a first color and wherein the second segments have a second color different from the first color.

8. The dental floss dispensing unit of claim 5, wherein the first segments are stiffer than the second segments, and wherein the metering element provides a greater magnitude of resistance against removal of the length of floss from the housing when the first segments are engaged with the metering element than when the second segments are engaged with the metering element.

9. The dental floss dispensing unit of claim 1, wherein the housing defines an aperture, and wherein the aperture provides access to the supply spool for manual rotation of the supply spool.

10. The dental floss dispensing unit of claim 9, wherein pulling the free end of the length of floss uncoils the length of floss from the supply spool, and wherein manually rotating the supply spool coils the length of floss onto the supply spool.

11. The dental floss dispensing unit of claim 1, further comprising a floss cutter coupled to the housing.

12. A dental floss dispensing unit comprising:
a housing;
a supply spool coupled to the housing and having a length of floss wound thereabout, the length of floss having a plurality of alternating and distinct first and second floss segments; and
a metering element engaging the length of floss and providing resistance to removal of the length of floss from the housing, wherein
a magnitude of the resistance changes as each floss segment moves into engagement with the metering element,
the metering element defines a serpentine path through which the length of floss extends,
the first floss segments are stiffer than the second floss segments, and
the magnitude of the resistance increases when the stiffer first floss segments are pulled through the serpentine path.

13. The dental floss dispensing unit of claim 12, wherein the resistance increases when a first floss segment moves into engagement with the metering element.

14. The dental floss dispensing unit of claim 12, wherein the first segments are stiffer than the second segments.

15. The dental floss dispensing unit of claim 12, wherein the supply spool rotates with respect to the housing as the length of floss is removed from the housing, and wherein the change in the magnitude of the resistance is independent from the rotation of the supply spool.

16. The dental floss dispensing unit of claim 12, wherein the metering element is biased into engagement with the length of floss and includes a groove through which the length of floss extends.

17. The dental floss dispensing unit of claim 16, wherein the first floss segments are more resistant to compression than the second floss segments, and wherein the magnitude of the resistance increases when the first floss segments are pulled through the groove.

18. A dental floss dispensing unit comprising:
a housing defining an interior volume and an opening communicating with the volume; and
a length of dental floss contained by the volume and having a free end extending through the opening, the length of dental floss including a plurality of alternating first and second segments, the first segments having a first physical property and the second segments having a second physical property different from the first physical property, wherein
the housing provides a tactilely detectable indexing as alternating first and second segments are withdrawn from the housing, and
the housing includes a reduced aperture through which the length of dental floss extends and that provides the tactilely detectable indexing.

19. The dental floss dispensing unit of claim 18, further comprising a spool rotatably mounted in the housing and about which the length of dental floss is wound.

20. A dental floss dispensing unit comprising:
a housing defining a volume;
a supply spool carried by the housing and positioned within the volume; and
a length of floss wound about the supply spool and having a free end extending from the housing, wherein
the free end can be pulled to unwind floss from the supply spool,
without manipulating the housing the supply spool is manually rotatable to rewind floss onto the supply spool,
the supply spool rotates with respect to the housing during removal of the length of floss from the housing, and
the magnitude of the resistance against removal of the length of floss from the housing is independent from rotation of the supply spool.

21. The dental floss dispensing unit of claim 20, wherein the housing defines an aperture, and wherein the supply spool is accessible by the user through the aperture.

22. The dental floss dispensing unit of claim 20, wherein the aperture exposes a front flange of the supply spool.

23. The dental floss dispensing unit of claim 20, wherein the supply spool includes a plurality of finger ridges.

* * * * *